(12) United States Patent
Mihara

(10) Patent No.: US 9,204,993 B2
(45) Date of Patent: Dec. 8, 2015

(54) TREATMENT OF DIVERTICULA

(71) Applicant: EMPIRE TECHNOLOGY DEVELOPMENT LLC, Wilmington, DE (US)

(72) Inventor: Masaaki Mihara, Chiba (JP)

(73) Assignee: EMPIRE TECHNOLOGY DEVELOPMENT LLC, Wilmington, DE (US)

( * ) Notice: Subject to any disclaimer, the term of this patent is extended or adjusted under 35 U.S.C. 154(b) by 282 days.

(21) Appl. No.: 13/991,405

(22) PCT Filed: Jan. 15, 2013

(86) PCT No.: PCT/US2013/021592
§ 371 (c)(1),
(2) Date: Jun. 3, 2013

(87) PCT Pub. No.: WO2014/112980
PCT Pub. Date: Jul. 24, 2014

(65) Prior Publication Data
US 2014/0200479 A1 Jul. 17, 2014

(51) Int. Cl.
*A61F 7/12* (2006.01)
*A61B 5/01* (2006.01)
*A61B 5/00* (2006.01)
*A61B 18/08* (2006.01)

(52) U.S. Cl.
CPC . *A61F 7/123* (2013.01); *A61B 5/01* (2013.01); *A61B 5/4836* (2013.01); *A61B 18/082* (2013.01); *A61B 2018/087* (2013.01)

(58) Field of Classification Search
CPC ........... A61F 7/12; A61F 7/123; A61F 7/126; A61F 2007/0028; A61F 2017/00818
USPC ...................................... 606/27–31
See application file for complete search history.

(56) References Cited

U.S. PATENT DOCUMENTS

| 6,110,168 A * | 8/2000 | Ginsburg .................. 606/27 |
| 6,306,154 B1 * | 10/2001 | Hudson et al. ................ 606/196 |
| 6,425,877 B1 | 7/2002 | Edwards |
| 7,112,196 B2 * | 9/2006 | Brosch et al. .................. 606/27 |

(Continued)

FOREIGN PATENT DOCUMENTS

| JP | 2005-261628 A | 9/2005 |
| WO | 99/40855 A1 | 8/1999 |
| WO | 03/020356 A1 | 3/2003 |

OTHER PUBLICATIONS

International Search Report and Written opinion dated Mar. 29, 2013 in application No. PCT/US2013/021592.

*Primary Examiner* — Max Hindenburg
(74) *Attorney, Agent, or Firm* — Maschoff Brennan

(57) ABSTRACT

Some embodiments described herein generally relate to apparatus and methods for treating diverticula. The diverticula may be present within a wall of a gastrointestinal organ, such as a colon, of a human or animal. In some examples, the apparatus may include a flexible conduit having a proximal end, a distal end, and a passageway therethrough, a balloon-forming chamber at the distal end of the flexible conduit, and at least one heating element positioned on an interior of the balloon-forming chamber. The apparatus may further include an endoscope in which the flexible conduit may be positioned such that the balloon-forming chamber extends from an end of the endoscope.

20 Claims, 15 Drawing Sheets

(56) References Cited

U.S. PATENT DOCUMENTS

| | | | |
|---|---|---|---|
| 8,025,638 B2* | 9/2011 | Arai et al. .................... 604/113 |
| 2002/0058960 A1 | 5/2002 | Hudson et al. |
| 2003/0069620 A1 | 4/2003 | Li |
| 2007/0287994 A1 | 12/2007 | Patel |
| 2009/0198095 A1 | 8/2009 | Acosta et al. |
| 2010/0087782 A1 | 4/2010 | Ghaffari et al. |
| 2010/0286680 A1 | 11/2010 | Kleyman |
| 2011/0082488 A1 | 4/2011 | Niazi |
| 2011/0251458 A1 | 10/2011 | Terliuc et al. |
| 2012/0226130 A1 | 9/2012 | Graff et al. |

* cited by examiner

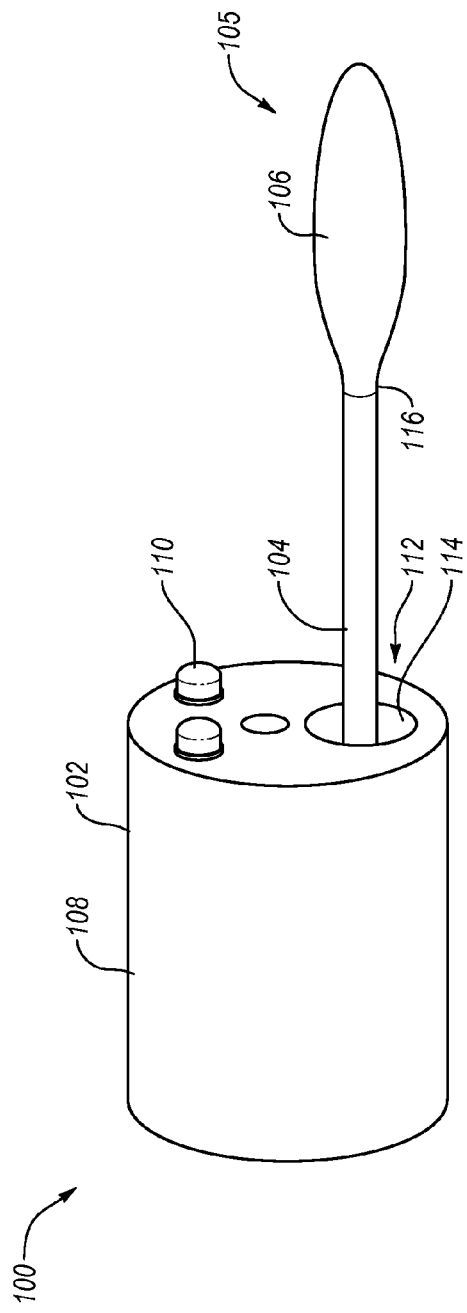
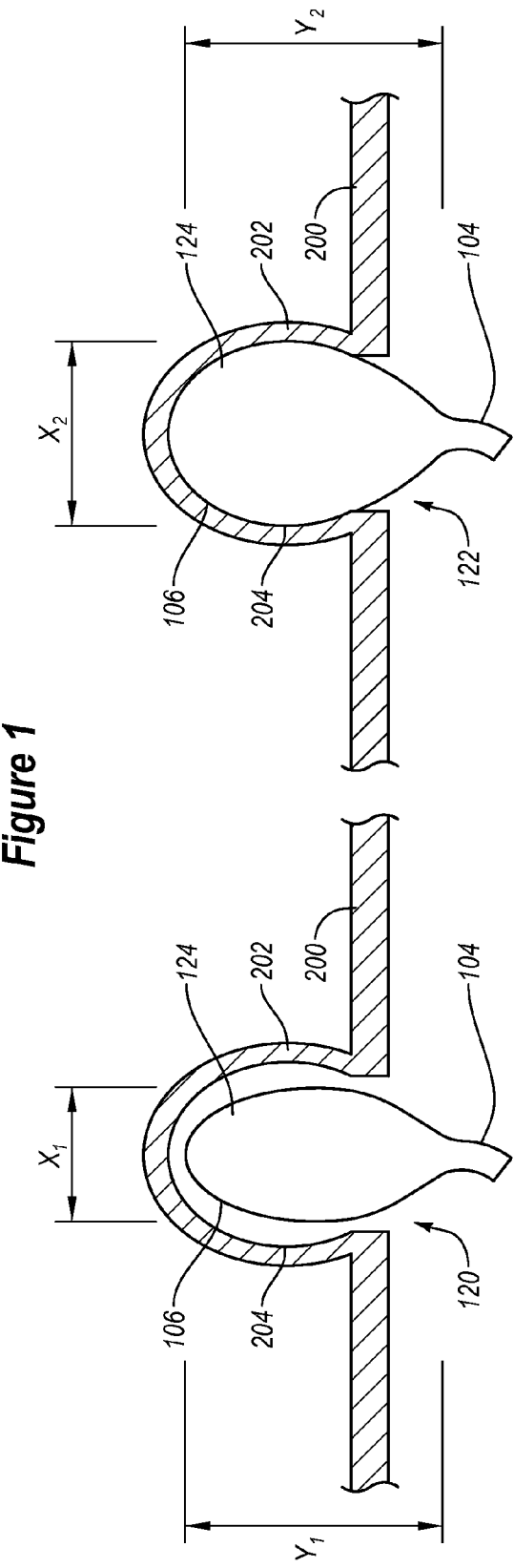

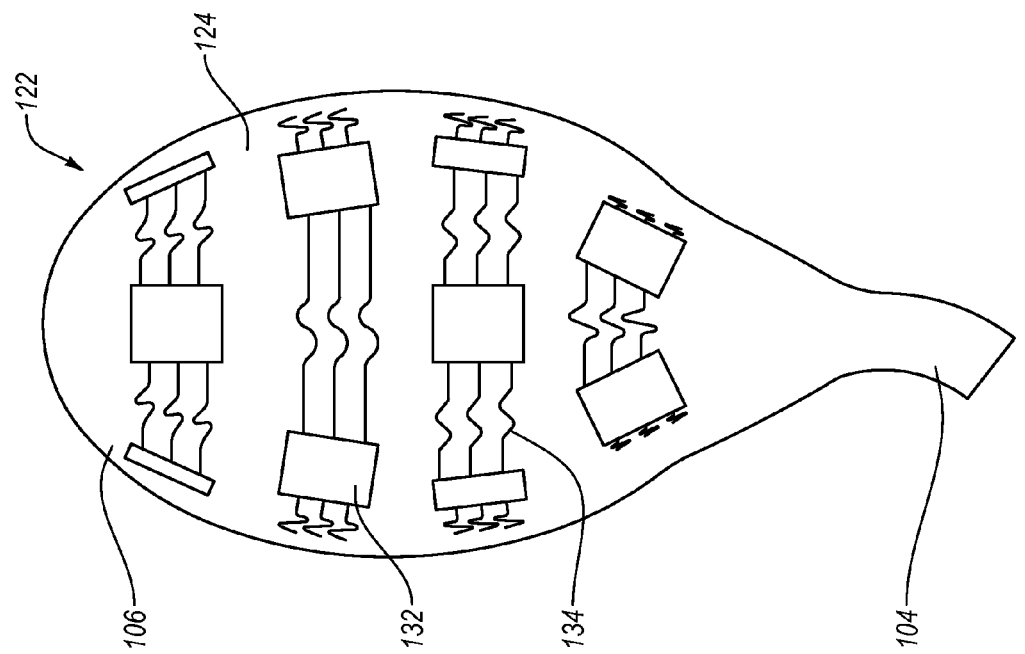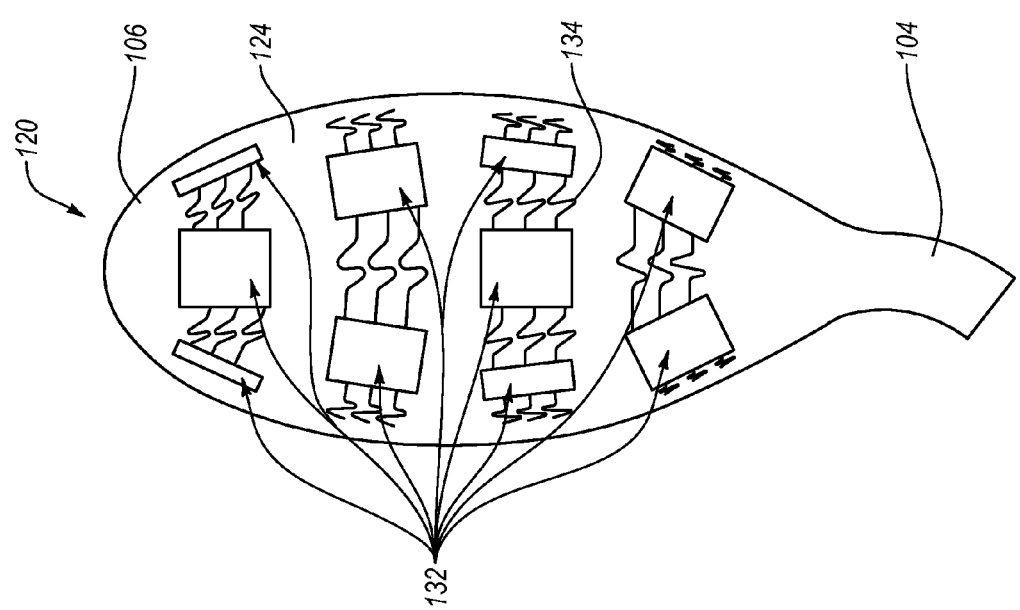
Figure 3

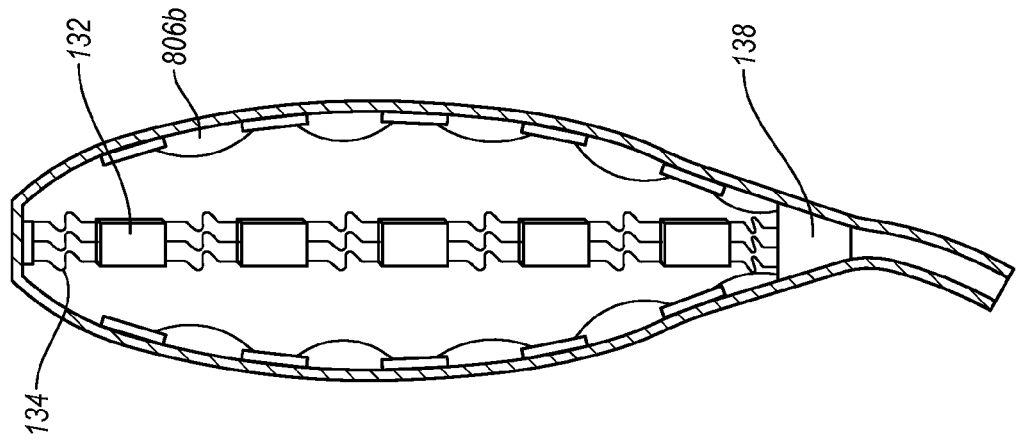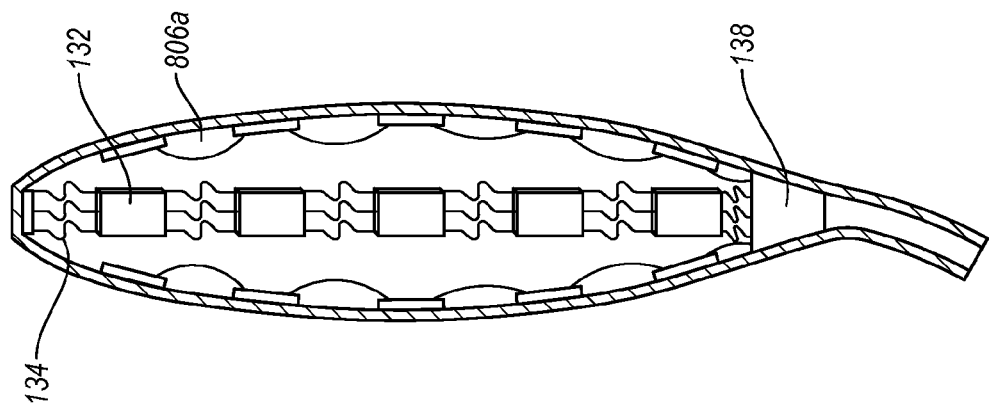
Figure 8

TREATMENT OF DIVERTICULA

BACKGROUND

Unless otherwise indicated herein, the materials described herein are not prior art to the claims in the present application and are not admitted to be prior art by inclusion in this section.

Diverticulitis of the colon is one of the most widespread diseases in developed Western countries. It is estimated that about 10 percent of Americans over the age of 40 and about 50 percent of Americans over the age of 60 have diverticulosis. Diverticulitis is caused by infection or inflammation of small pouches in the lining of the colon that bulge outward through weak spots. Such pouches are referred to as diverticula. Inflammation of the diverticula may lead to bleeding, infections, small tears, perforations, or blockages in the colon.

In the absence of treatment, complications associated with diverticulitis may progress causing serious illness. For example, an infection may lead to formation of an abscess in the wall of the colon that, if left untreated, may require further medical treatment. Infected diverticula may develop perforations, rupture, or break open causing intestinal contents to leak or spill out into the surrounding peritoneal cavity which may lead to a serious infection, or even sepsis. For example, the perforations may result in leakage of pus and other intestinal fluids into the surrounding peritoneal cavity forming an intraabdominal abscess, a condition referred to as peritonitis. Peritonitis requires immediate surgery to clean the peritoneal cavity and remove the damaged part of the colon, or it may be fatal.

The main symptomatic treatment of diverticulosis of the colon has involved suppressing inflammation and bleeding using anti-inflammation drugs or antibiotics. In the event of repeated recurrence of diverticulosis, however, surgical removal of the diverticulum is unavoidable. This is a considerable burden on the patient and raises issues such as anti-infection measures after the operation. Furthermore, in the case of surgery in which the diverticulum is removed by using a colonoscope, there has been a risk that the contents of the colon might leak out from the removed portion into the abdominal cavity, resulting in severe peritonitis. Furthermore, removing sections of the colon can impair the natural functioning of the colon resulting in undesirable side effects, such as irregular bowel movements, diarrhea, bladder complications, etc.

SUMMARY

The technologies described herein generally relate to apparatus and methods for treating diverticula.

In some examples, an apparatus for treating diverticula is disclosed. The apparatus may include a flexible conduit having a proximal end, a distal end and a passageway therethrough, a balloon-forming chamber at the distal end of the flexible conduit, and a plurality of integrated circuit elements positioned on walls of the balloon-forming chamber. As a non-limiting example, each of the integrated circuit elements may include a temperature sensor and a heating element, such as a MOSFET device. The integrated circuit elements may be positioned on an interior surface of the balloon-forming chamber.

In some examples, a medical device for treating diverticula is disclosed. Such a medical device may include an elongated shaft, a conduit having a hollow interior chamber extending along at least a portion of a length of the elongated shaft, a balloon-forming chamber positioned at a distal end of the endoscope, an opening of the balloon-forming chamber in communication with the hollow interior chamber of the conduit, and a plurality of integrated circuit elements positioned on surfaces of the balloon-forming chamber, each of the integrated circuits of the plurality including at least one heating element and a temperature sensor.

In some examples, methods of treating diverticula are disclosed. Such a method may include, for example, introducing an endoscope into a colon, the endoscope having an inflatable bladder at a distal end, the inflatable bladder in fluid communication with a passageway extending along the endoscope, positioning the inflatable bladder in a diverticulum within a wall of the colon, introducing a fluid into the inflatable bladder to expand the inflatable bladder, analyzing temperature data collected by temperature sensors of each of a plurality of integrated circuit elements on a wall of the inflatable bladder to determine at least one region of the inflatable bladder in contact with the diverticulum and causing a heating element of at least one integrated circuit element in the at least one region to generate heat. For example, the at least one region of the inflatable bladder may be in contact with inflamed or infected tissue of the diverticulum.

The foregoing summary is illustrative only and is not intended to be in any way limiting. In addition to the illustrative aspects, embodiments, and features described above, further aspects, embodiments, and features will become apparent by reference to the drawings and the following detailed description.

BRIEF DESCRIPTION OF THE FIGURES

In the drawings:

FIG. 1 illustrates a perspective view of an embodiment of a medical device for treating diverticula;

FIG. 2 illustrates a cross-sectional view of an embodiment of an apparatus that may be used in the medical device of FIG. 1 positioned in a diverticulum;

FIG. 3 illustrates an enlarged view of an interior of the apparatus of FIG. 2;

FIG. 8 illustrates a cross-sectional view of another embodiment of an apparatus that may be used in the medical device of FIG. 1;

DETAILED DESCRIPTION

Figure 4:
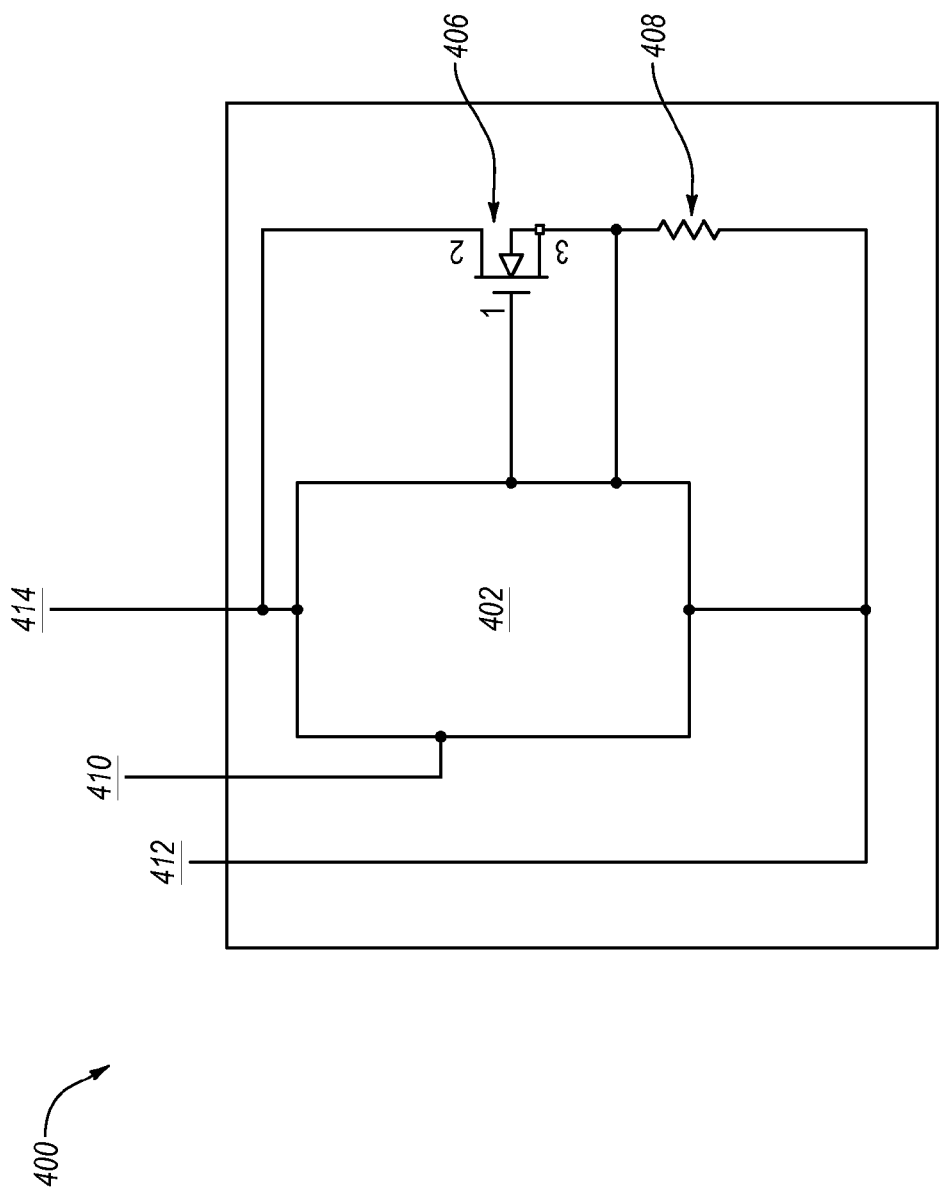
FIG. 4 is an electrical diagram of an embodiment of an integrated circuit that may be used in the apparatus of FIGS. 1 through 3.

In the following detailed description, reference is made to the accompanying drawings, which form a part hereof. In the drawings, similar symbols typically identify similar components, unless context dictates otherwise. The illustrative embodiments described in the detailed description, drawings, and claims are not meant to be limiting. Other embodiments may be utilized, and other changes may be made, without departing from the spirit or scope of the subject matter presented herein. It will be readily understood that the aspects of the present disclosure, as generally described herein, and illustrated in the figures, can be arranged, substituted, combined, separated, and designed in a wide variety of different configurations, all of which are explicitly contemplated herein.

Some embodiments described herein generally relate to apparatus and methods for treating diverticula. As used herein, the term "diverticula" and "diverticulum" may refer to a sac- or pouch-like opening from a hollow organ or structure, such as the colon. Such diverticula may become inflamed or infected, may develop granulomas or may bleed. The apparatus and methods disclosed herein enable identification of inflamed or infected tissue within the diverticulum and localized heat treatment of such tissues. The heat treatment may denature proteins in the tissue to promote healing of the tissue and the granulomas.

For example, the apparatus may include an endoscope having attached at its distal end a balloon-forming chamber whose size is freely variable in accordance with the shape of the diverticulum. The balloon-forming chamber may include multiple integrated circuit chips having heat generators whose heating temperature and heating period can be controlled by an external device. For example, the integrated circuit chips may be positioned on or within walls of the balloon-forming chamber, such as on an inner surface of the balloon-forming chamber. The balloon-forming chamber may be inserted into a diverticulum and expanded such that at least one of the multiple integrated circuit chips contacts a surface of the diverticulum. Information about contact with the diverticulum may be collected and transmitted from the integrated circuit chips in the expanded balloon-forming chamber to an external device. The external device may analyze the information and generate instructions for heating selected integrated circuit chips at specified temperatures and for a specific period of time. Thus, it is possible to heat the surface of the expanded balloon-forming chamber under precise temperature management to provide localized heat generation. Heating the surface of the diverticulum tissue, which will promote formation of healing granuloma on the tissue, may reduce or eliminate inflammation and bleeding, which may reduce symptoms associated with diverticulosis or may cure diverticulosis.

The apparatus and methods described herein provide detection and localized treatment of diseased tissue within diverticula. Integrated circuit chips distributed inside the balloon-forming chamber are utilized to enable a specific, diseased region of the diverticulum to be heated at a precise temperature and for a precise period of time.

FIG. 1 illustrates a perspective view of an embodiment of a medical device for treating diverticula, arranged in accordance with at least some embodiments described herein. The medical device 100 may be configured to treat diverticula in organs such as the colon.

The medical device 100 may include an endoscope 102, a flexible conduit 104, and an apparatus 105 including a balloon-forming chamber 106 and integrated circuit elements (not shown). The endoscope 102 may include an elongated shaft 108 and an optical imaging system 110 positioned at a distal end 112 of the elongated shaft 108. The distal end 112 of the endoscope may be configured for introduction into a cavity of a body of a human or animal. The endoscope 102 may include a passageway 114 extending along at least a portion of a length of the elongated shaft 108. The passageway 114 may be sized and configured to house the flexible conduit 104.

The flexible conduit 104 may be positioned within the passageway 114 of the endoscope 102. The flexible conduit 104 may have a hollow interior portion for conveying air or other fluids. The flexible conduit 104 may have cross-sectional dimensions of less than about 10 mm and, more particularly, between about 0.1 mm and about 3 mm. For example, in embodiments in which the flexible conduit 104 has an elongated cylindrical shape, the flexible conduit 104 may have a diameter of between about 0.5 mm and about 2 mm.

The balloon-forming chamber 106 may be positioned at an end of the flexible conduit 104. For example, the balloon-forming chamber 106 may be positioned on a portion of the flexible conduit 104 protruding out of the passageway 114 of the endoscope 102. The balloon-forming chamber 106 may be, for example, a flexible, inflatable bladder formed from an elastic material. The balloon-forming chamber 106 may be attached or fused to the flexible conduit 104 at an attachment point 116, or may integrally be formed with the flexible conduit 104 such that the balloon-forming chamber 106 and the flexible conduit 104 form a unitary structure.

The flexible conduit 104 and the balloon-forming chamber 106 may be formed from a material that exhibits elasticity, biocompatibility, and heat resistance. As used herein, the term "biocompatible" may refer to any material compatible with living tissue, any material that does not cause severe toxicity, severe adverse biological reaction, or lethality in a human or animal. The term "biocompatible" does not exclude materials that elicit biological reaction that is not adverse. The material may be resistant to melting, ignition, and/or decomposition at temperatures between about 40° C. and about 200° C. As a non-limiting example, the flexible conduit 104 and the balloon-forming chamber 106 may be formed from a silicone-containing material, such as silicone rubber, or from a fluoro-rubber. As another non-limiting example, the flexible conduit 104 and the balloon-forming chamber 106 may be formed from polymer material or a thermoplastic material having a high elasticity. The flexible conduit 104 and the balloon-forming chamber 106 may be formed having substantially smooth outer surfaces to enable the medical device 100 to be more easily and comfortably inserted.

FIG. 2 illustrates a cross-sectional view of an embodiment of an apparatus of the medical device of FIG. 1, arranged in accordance with at least some embodiments described herein. The balloon-forming chamber 106 may be positioned within a diverticulum 202 in an organ such as a colon 200. For example, the endoscope 102 having the balloon-forming chamber 106 positioned at the distal end 112 may be introduced into the colon 200 and the optical imaging system 110 may be utilized to position the balloon-forming chamber 106 within the diverticulum 202.

A size of the balloon may be freely variable to conform to a shape of the diverticulum 202 in the colon 200. The balloon-forming chamber 106 may have a static state 120 and an expanded state 122. A fluid, such as air, may be introduced into the balloon-forming chamber 106 through the flexible conduit 104. As the fluid is introduced into the balloon-forming chamber 106, the balloon-forming chamber 106 may transition from the static state 120 to the expanded state 122 as a wall 124 of the balloon-forming chamber 106 expands outward. For example, the balloon-forming chamber 106 may have an annular cross section and the term "wall" may refer to a thickness of the annular cross section. The wall 124 may be formed from the material that exhibits elasticity, biocompatibility, and heat-resistance (e.g., silicone rubber, fluoro-rubber, etc.), for example. The balloon-forming chamber 106 may be expanded by introducing a fluid, such as air, into the balloon-forming chamber 106 through the flexible conduit 104.

The fluid may be introduced into the balloon-forming chamber 106 until at least one region of the wall of the balloon-forming chamber 106 contacts an inner surface 204 of the diverticulum 202. For example, the balloon-forming chamber 106 may be expanded by filling the balloon-forming chamber 106 with the fluid such that at least a portion of the balloon-forming chamber 106 substantially fills the diverticulum 202 and outer surfaces of the wall 124 of the balloon-forming chamber 106 contact the inner surface 204 of the diverticulum 202.

The balloon-forming chamber 106 may, thus, be configured to conform to the inner surface 204 of the diverticulum 202 in the expanded state 122. In the static state 120, the balloon-forming chamber 106 may have a first dimension $X_1$ in a first direction and second dimension $Y_1$ in a second direction, the second direction substantially perpendicular to the first direction. An expansion ratio of the balloon-forming chamber 106 may be greater in the first direction than in the second direction. As used herein, the term "expansion ratio" may refer to a ratio of the expansion along a transverse cross section in a first direction compared to the expansion along a transverse cross section in the second, perpendicular direction. The first dimension $X_2$ of the balloon-forming chamber 106 may be about 2 to 3 times greater in the expanded state 122 than a first dimension $X_1$ in the static state 120. As a non-limiting example, the first dimension $X_1$ of the balloon-forming chamber 106 in the static state 120 may be between about 0.5 mm and about 8 mm and, more particularly, between about 1 mm and about 4 mm and, more particularly, between about 2 mm and about 3 mm. As a non-limiting example, the first dimension $X_2$ of the balloon-forming chamber 106 in the expanded state 122 may be between about 1 mm and about 10 mm and, more particularly, between about 2 mm and about 6 mm and, more particularly, between about 3 mm and about 5 mm. For example, the first dimension $X_1$ may be about 2 mm in the static state 120 and the first dimension $X_2$ may be about 4 mm in the expanded state 122.

FIG. 3 illustrates an enlarged view of an interior of the apparatus of FIG. 2, arranged in accordance with at least some embodiments described herein. One or more integrated circuit elements 132 may be positioned on or within the wall of the balloon-forming chamber 106. Each of the integrated circuit elements 132 may include a heating element and a temperature sensor, for example. While the integrated circuit elements 132 are illustrated in FIG. 3 as being positioned on an interior surface of the balloon-forming chamber 106, the integrated circuit elements 132 may be positioned between layers of material forming the wall 124 of the balloon-forming chamber 106 or on an outer surface of the wall 124 of the balloon-forming chamber 106. As a non-limiting example, the integrated circuit elements 132 may be positioned on a support that may be attached to the interior surface of the wall 124 of the balloon-forming chamber 106. As another non-limiting example, the integrated circuit elements 132 may be embedded within the wall 124 of the balloon-forming chamber 106. The integrated circuit elements 132 may be positioned to circumscribe the wall 124 of the balloon-forming chamber 106. For example, the integrated circuit elements 132 may be distributed across the wall 124 of the balloon-forming chamber 106 by substantially equal distances, or may be positioned at particular areas of the wall 124 of the balloon-forming chamber 106. As a non-limiting example, the integrated circuit elements 132 may be positioned in a region at or near a terminus of the balloon-forming chamber 106.

Each of the integrated circuit elements 132 may be communicatively coupled to one or more adjacent heating elements by interconnects 134. In some embodiments, each of the integrated circuit elements 132 may be formed as an integrated circuit device, and the integrated circuit devices may be electrically coupled to one another via the interconnects 134. For example, the interconnects 134 may be conductive wires having a configuration that enables the conductive wires to contract and extend as distance between the adjacent integrated circuit elements 132 changes as the balloon-forming chamber 106 moves between the static state 120 and the expanded state 122. While the interconnects 134 are illustrated in FIG. 3 as having an S-shape, it is to be understood that the interconnects 134 may have any shape that enables the interconnects 134 to contract and extend, such as an L-shape, a U-shape, or a W-shape, for example. The interconnects 134 may each have a length greater than a distance between the integrated circuit elements 132 when the balloon-forming chamber 106 is in the static state 120 such that, upon expansion of the balloon-forming chamber 106, the interconnects 134 extend to maintain the communicative coupling between the adjacent integrated circuit elements 132.

FIG. 4 is an electrical diagram of an embodiment of an integrated circuit that may be used in the apparatus of FIGS. 1 through 3, arranged in accordance with at least some embodiments described herein. The integrated circuit 400 may include a control circuit 402 with a temperature sensor, a heating element 406 and a current sensing resistor 408. The integrated circuit 400 may be used as the integrated circuit elements 132 of the medical device 100 described with respect to FIG. 3. For example, the control circuit 402 may be configured to detect a temperature of a surface of the balloon-forming chamber 106 adjacent the integrated circuit 400. The heating element 406 may include a power semiconductor switch, such as a metal-oxide-semiconductor field effect transistor (MOSFET). While the heating element 406 is illustrated as a MOSFET device within the integrated circuit 400, the heating element 406 may be any device capable of generating heat. For example, the heating element 406 may generate temperatures of between about 40° C. and about 200° C. and, more particularly, between about 60° C. and about 90° C.

The current sensing resistor 408 may detect a current of the heating element 406. The control circuit 402 detects a voltage occurring in the current sensing resistor 408. The control circuit 402 detects overcurrent in the heating element 406 to protect the integrated circuit 400. When the heating element 406 is heated, the current detected by the current sensing resistor 408 may be fed back to the control circuit 402 for the heating element 406.

The integrated circuit 400 may have dimensions of between about 0.5 mm and about 3 mm. For example, the integrated circuit 400 may have a first dimension of between about 0.5 mm and about 3 mm and a second dimension of between about 1 mm and about 3 mm.

In embodiments in which the heating element 406 includes a MOSFET, a gate 1 of the MOSFET may be operably coupled to the control circuit 402 to turn the MOSFET between an "on" state and an "off" state based on information generated by the temperature sensor of the control circuit 402. As will be discussed, an external device may be used to control the MOSFET by switching the MOSFET between the on and off states. The external device may be coupled to the integrated circuit 400 by a control signal line 410, and may receive information related to the temperature detected by the control circuit 402. The information may be used to determine if the integrated circuit 400 should be heated using the heating element 406, and the external device may transmit a signal to the control circuit 402 through the control signal line 410 to turn the heating element 406 on or off.

The MOSFET may also include a drain 2 and a source 3. The drain 2 of the MOSFET may be operably coupled to a power supply line 414 and the source 3 may be connected to the control circuit 402 and a ground line 412 with the current sensing resistor 408 therebetween. The source 3 is coupled to the control circuit 402 and the current sensing resistor 408 is connected to the ground line 412.

The integrated circuit 400 is, thus, configured as a monolithic integrated circuit having the control circuit 402, the heating element 406 and the current sensing resistor 408 on a single integrated circuit chip. By integrating the heating element 406 and temperature sensor of the control circuit 402 in a single circuit, such as integrated circuit 400, the heat generated by the integrated circuit 400 may be controlled independently. For example, the temperature of a region of the balloon-forming chamber 106 proximate to the integrated circuit 400 may be monitored as the heating element 406 is used to generate heat. The information gathered by the temperature sensor of the control circuit 402 may be used to control the heating element 406 to maintain a specific temperature for a specific period of time.

Figure 5:
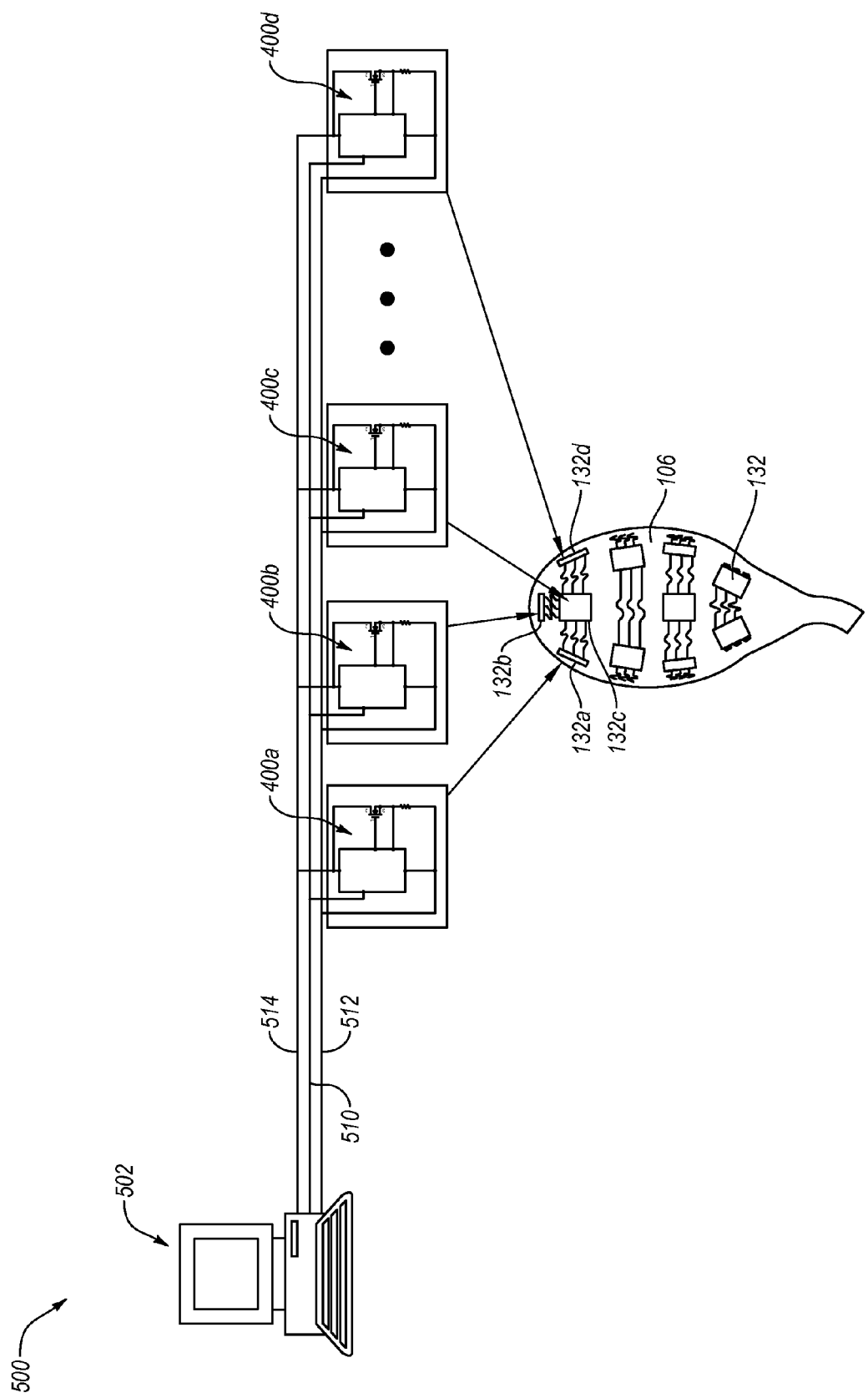
FIG. 5 illustrates an embodiment of a computing system that may be used in conjunction with the apparatus of FIGS. 1 through 3.

FIG. 5 illustrates an embodiment of a computing system that may be used in conjunction with the apparatus of FIGS. 1 through 3, arranged in accordance with at least some embodiments described herein. The computing system 500 may include an external device 502, which is operably coupled to one or more of the integrated circuit elements 132 of the balloon-forming chamber 106. Each of the integrated circuit elements 132 may include a temperature sensor integrated with a heating element. As a non-limiting example, the integrated circuit elements 132 may each include an integrated circuit including a temperature sensor and a heating element, such as the integrated circuit 400 described with respect to FIG. 4. For the purposes of illustration, the integrated circuit elements 132a, 132b, 132c, and 132d and integrated circuits 400a, 400b, 400c, and 400d are shown in detail. It will be understood that the balloon-forming chamber 106 may include any number of integrated circuit elements 132 having the configuration described with respect to the integrated circuit elements 132a, 132b, 132c, and 132d.

The computing system 500 may be operably coupled to each of the integrated circuit elements 132a, 132b, 132c, and 132d to monitor and control a temperature of the balloon-forming chamber 106. In embodiments in which the integrated circuit elements 132a, 132b, 132c, and 132d each include a MOSFET as a heating element, the computing system 500 may be operably coupled with the MOSFET such that the computing system 500 may be used to switch the MOSFET between on and off states.

Each of the integrated circuits 400a, 400b, 400c, and 400d may be operably coupled to the external device 502 by electrical lines, such as a communication line 510, a ground line 512, and a power line 514. For example, the communication line 510 may couple the external device 502 to the control signal line 410 of each of the integrated circuits 400a, 400b, 400c, and 400d, the ground line 512 may couple the external device 502 to the ground line 412 of each of the integrated circuits 400a, 400b, 400c, and 400d and the power line 514 may couple the external device 502 to the power line 414 of each of the integrated circuits 400a, 400b, 400c, and 400d. The computing system 500 may receive temperature data from the control circuit 402 of each of the integrated circuits 400a, 400b, 400c, and 400d, which may be transmitted through the control signal line 410 and the communication line 510. For example, the control circuit 402 including the temperature sensor may detect the temperature of each of the integrated circuits 400a, 400b, 400c, and 400d. The temperature may be transmitted to the external device 502 via the communication line 510 coupled to the control signal line 410 and temperature data for each of the integrated circuits 400a, 400b, 400c, and 400d may be analyzed to determine which integrated circuit elements 132a, 132b, 132c, and 132d are positioned in regions of the balloon-forming chamber 106 that may respond to heat treatment.

As a non-limiting example, the temperature data may be analyzed to determine surfaces of the balloon-forming chamber 106 in contact with the diverticulum. As another non-limiting example, the temperature data may be analyzed to determine surfaces of the balloon-forming chamber 106 in contact with inflamed or infected tissue within the diverticulum. For example, the computing system 500 may be configured to determine whether the temperature detected by the temperature sensor of each of the integrated circuits 400a, 400b, 400c, and 400d is greater than or equal to a specified temperature or is within a specified temperature range. The specified temperature may be, for example, between about 35° C. and about 40° C. and more particularly, between about 36.8° C. and about 38° C. and, more particularly, about 37° C. The temperature data for each of the integrated circuits 400a, 400b, 400c, and 400d may be analyzed to determine portions of the diverticulum having a temperature indicating a fever, or the presence of the inflamed or infected tissue within the diverticulum. The computing system 500 may then determine which of the integrated circuit elements 132a, 132b, 132c, and 132d should be heated to treat the diverticulum.

The integrated circuit elements 132 are connected to one another in parallel inside the balloon-forming chamber 106, which enables communication with the external device 502 using serial data. This arrangement enables temperature data from each of the integrated circuit elements 132 to be transmitted to the external device 502, and enables transmission of a signal from the external device 502 to heat one or more selected integrated circuit elements 132.

Figure 6:
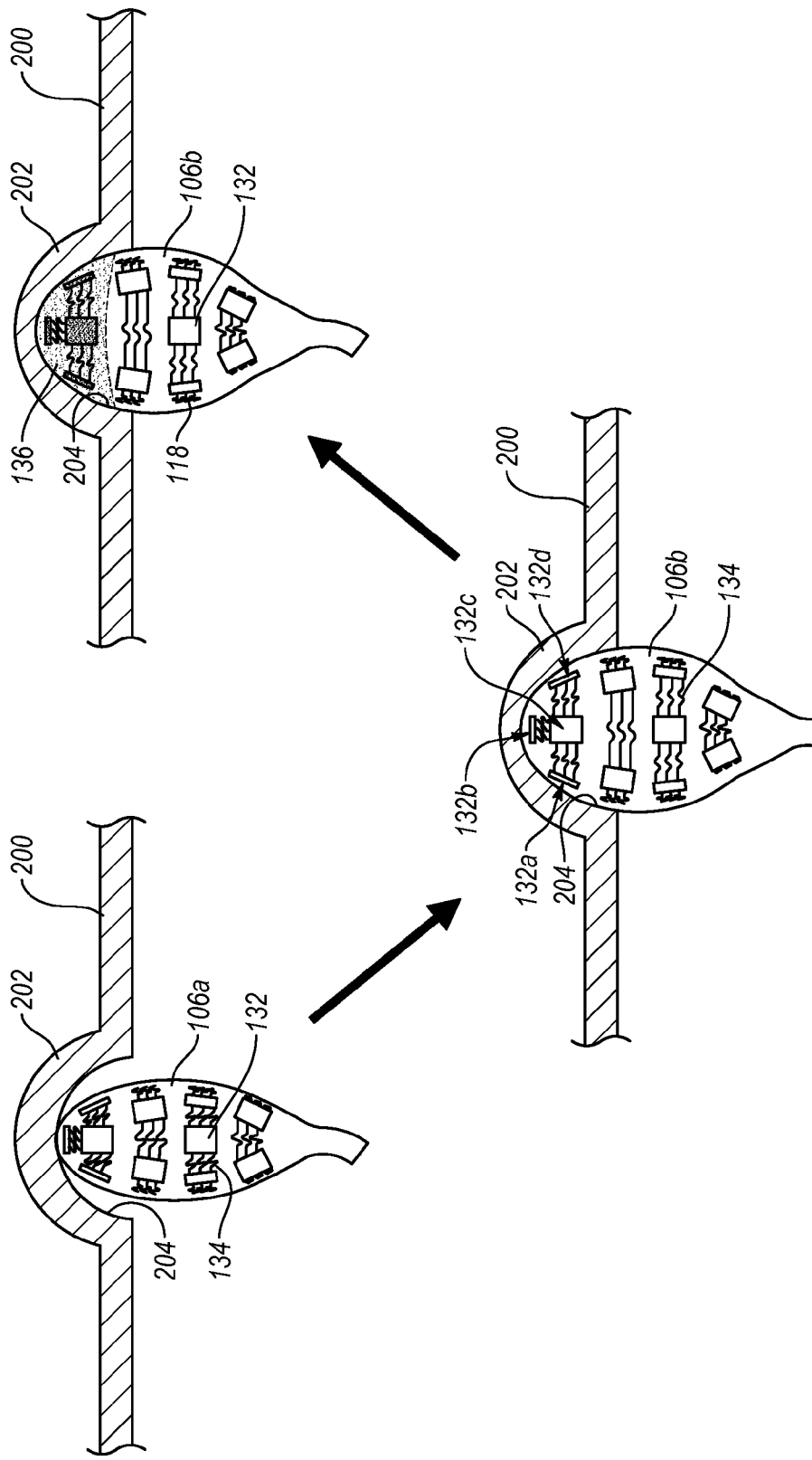
FIG. 6 illustrates another embodiment of an apparatus including integrated circuit elements positioned in a diverticulum.

FIG. 6 illustrates another embodiment of an apparatus including integrated circuit elements in use in treating a diverticulum, arranged in accordance with at least some embodiments described herein. The balloon-forming chamber 106a may be introduced into a diverticulum 202 in an organ, such as in a wall of a colon 200. The integrated circuit elements 132 on or within the walls of the inflated balloon-forming chamber 106b may be used to generate and apply heat to localized areas of the diverticulum 202 in the colon 200. As a non-limiting example, the balloon-forming chamber 106a may be positioned at the end of a medical device, such as the endoscope 102 of FIG. 1, which may be introduced into the colon 200 and positioned such that at least a portion of the balloon-forming chamber 106a is positioned within the diverticulum 202 in the colon 200.

The balloon-forming chamber 106a may then be expanded, for example, by introducing air or another fluid into the balloon-forming chamber 106a to form an inflated balloon-forming chamber 106b. At least a portion of an outer surface of the inflated balloon-forming chamber 106b may be in close proximity to or contact with the inner surface 204 of the diverticulum 202. The integrated circuit elements 132 may be positioned on the interior surfaces of the balloon-forming chamber 106 such that the integrated circuit elements 132 do not directly contact the inner surface 204 of the diverticulum 202. As the walls of the balloon-forming chamber 106a expand to form the inflated balloon-forming chamber 106b, the interconnects 134 between the integrated circuit elements 132 may extend to maintain the electrical coupling between the integrated circuit elements 132. For example, the air may be fed into the inflated balloon-forming chamber 106b until the outer surface of the inflated balloon-forming chamber 106b nearly at least partially, or completely, comes into contact with the inner surface 204 of the diverticulum 202, such that the temperature sensors of the integrated circuit elements 132 may obtain and send temperature data to the external device 502. The integrated circuit elements 132 may be positioned on the interior surfaces of the balloon-forming chamber 106 and, thus, the wall of the balloon-forming chamber 106 is disposed between the integrated circuit elements 132 and the inner surface 204 of the diverticulum 202 such that the integrated circuit elements 132 are not in direct contact with the inner surface 204. For example, the integrated circuit elements 132 may detect a temperature of a surrounding environment. The temperature data collected by each of the integrated circuit elements 132 may be analyzed to determine which of the integrated circuit elements 132 may be used to apply heat to treat the diverticulum 202.

Based on the temperature data obtained by the integrated circuit elements 132, a heating temperature and a heating period may be determined for a designated region of the inflated balloon-forming chamber 106b. For example, an image of the surface of the diverticulum 202 in contact with the inflated balloon-forming chamber 106b may be captured and displayed on a monitor of the external device 502 to determine one or more regions 136 of the inflated balloon-forming chamber 106b that may be heated to treat the diverticulum 202. For example, the image may be captured using the optical imaging system 110 of the endoscope 102 described with respect to FIG. 1.

As previously discussed, each of the integrated circuit elements 132 may be operably coupled to an external computing device which may receive and analyze the temperature data generated by each of the integrated circuit elements 132. As a non-limiting example, the temperature detected by each of the integrated circuit elements 132 may be analyzed to determine the region 136 of the inflated balloon-forming chamber 106b in contact with the diverticulum 202. As another non-limiting example, the temperature of each of the integrated circuit elements 132 may be used to determine the region 136 within the diverticulum 202 including inflamed or diseased tissue. For example, an increased temperature may be detected by one or more of the integrated circuit elements 132 and may indicate the presence of inflamed tissue or a fever indicative of an infection in the region 136 of the diverticulum 202 adjacent to the one or more integrated circuit elements 132.

The temperature data collected by each of the integrated circuit elements 132 may, thus, be used to determine which of the integrated circuit elements 132 may be used to apply heat to the diverticulum 202. As a non-limiting example, each of the integrated circuit elements 132a, 132b, 132c, and 132d in the region 136 of the inflated balloon-forming chamber 106b determined to be in contact with the diverticulum 202 may be used to apply heat to the inner surface 204 of the diverticulum 202. As another non-limiting example, the integrated circuit elements 132a, 133b, 132c, and 132d may be those positioned within the region 136 of the inflated balloon-forming chamber 106b in contact with the diverticulum 202, as determined by temperature data collected by the integrated circuit elements 132. The integrated circuit elements 132a, 133b, 132c, and 132d within the region 136 may be used to generate heat to treat the diverticulum 202.

For example, heat may be applied to tissue deep inside the diverticulum 202 and tissue at an interface between a wall of the colon 200 and the diverticulum 202 may be excluded from heating. For example, by setting a heating profile in advance with a temperature of between about 60° C. and about 90° C. and a heating period of between about 2 seconds and about 10 seconds, heating of the surface of the diverticulum 202 may be localized. Accordingly, it is possible to safely treat the diverticulum 202 in a short time period.

Figure 7:
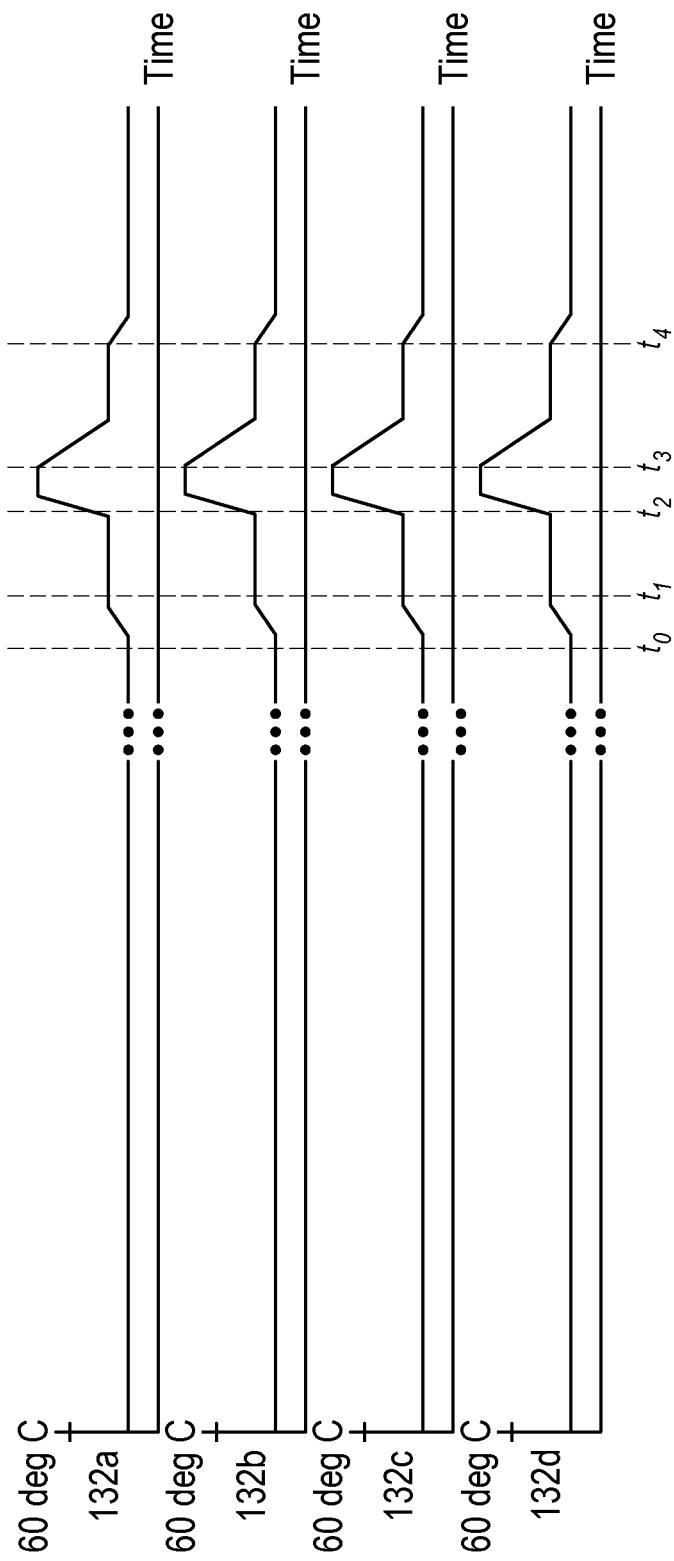
FIG. 7 illustrates an embodiment of a thermal profile for each integrated circuit element of the apparatus of FIG. 6.

FIG. 7 illustrates an embodiment of a thermal profile for each integrated circuit element of the apparatus of FIG. 6, arranged in accordance with at least some embodiments described herein. The thermal profile shows a temperature generated by the integrated circuit elements 132a, 132b, 132c, and 132d over time. The balloon-forming chamber 106 may be positioned in the diverticulum 202 as shown in FIGS. 2 and 6, for example. At time $t_0$, the fluid may be introduced into the balloon-forming chamber 106 causing expansion of the balloon-forming chamber 106 such that the outer surfaces of the balloon-forming chamber 106 contact the tissue within the diverticulum 202. The integrated circuit elements 132a, 132b, 132c, and 132d may detect contact with the tissue within the diverticulum 202 at time $t_1$. For example, the integrated circuit elements 132a, 132b, 132c, and 132d may detect a specified temperature, as illustrated by the first peak in the thermal profile.

At time $t_2$, the heating element within each of integrated circuit elements 132a, 132b, 132c, and 132d may generate heat in response to detection of the specified temperature, as illustrated by the second peak of the thermal profile. For example, a temperature greater than or equal to a body temperature of the human or animal may be detected by the integrated circuit elements 132a, 132b, 132c, and 132d. Thus, the integrated circuit elements 132a, 132b, 132c, and 132d may detect a temperature of greater than or equal to about 37° C., and may then be heated to treat the tissue of the diverticulum. As a non-limiting example, the integrated circuit elements 132a, 132b, 132c, and 132d may be heated to temperatures of greater than or equal to about 60° C. to provide localized heating of the tissue or granulomas in contact with or proximate to the integrated circuit elements 132. The localized heating may enable denaturation of the proteins within the tissue or granulomas which may promote healing of the diverticulum. The integrated circuit elements 132 that do not detect a temperature greater than or equal to the specified temperature may not be activated to generate heat.

The integrated circuit elements 132a, 132b, 132c, and 132d may be controlled to generate the heat for a specified time period. For example, the heating elements of each of the integrated circuit elements 132a, 132b, 132c, and 132d may provide heat for a time period of between about 1 second and about 30 seconds and, more particularly, between about 5 seconds and about 20 seconds and, more particularly, between about 10 seconds and about 15 seconds.

At time $t_3$, the integrated circuit elements 132a, 132b, 132c, and 132d may be controlled to stop generating the heat by turning the heating element off. For example, the temperature of the balloon-forming chamber 106 may be reduced to about the body temperature, such as about 37° C., at which point the inflated balloon-forming chamber 106 is still in contact with the tissue of the diverticulum. The balloon-forming chamber 106 may then be deflated by, for example, releasing the fluid from the balloon-forming chamber 106 at time $t_4$.

FIG. 8 illustrates a cross-sectional view of another embodiment of an apparatus that may be used in the medical device of FIG. 1, arranged in accordance with at least some embodiments described herein. A balloon-forming chamber 806a may be sized and configured to substantially conform to diverticula having varied sizes and shapes. For example, the balloon-forming chamber 806a may be configured to fit within a diverticulum having a long, thin shape. The interconnects 134 coupling adjacent integrated circuit elements 132 may be positioned in a direction having a smaller expansion ratio. For example, the integrated circuit elements 132 may be positioned in multiple rows along a length of the balloon-forming chamber 806a. The balloon-forming chamber 806a may be inflated with air or another fluid to form an inflated balloon-forming chamber 806b. As the balloon-forming chamber 806a is inflated, the interconnects 134 may expand such that the integrated circuit elements 132 remain coupled by the interconnects 134. Each of the interconnects 134 may be coupled to a contact point 138, which may be positioned at a base of the balloon-forming chamber 806a.

Figure 9A:
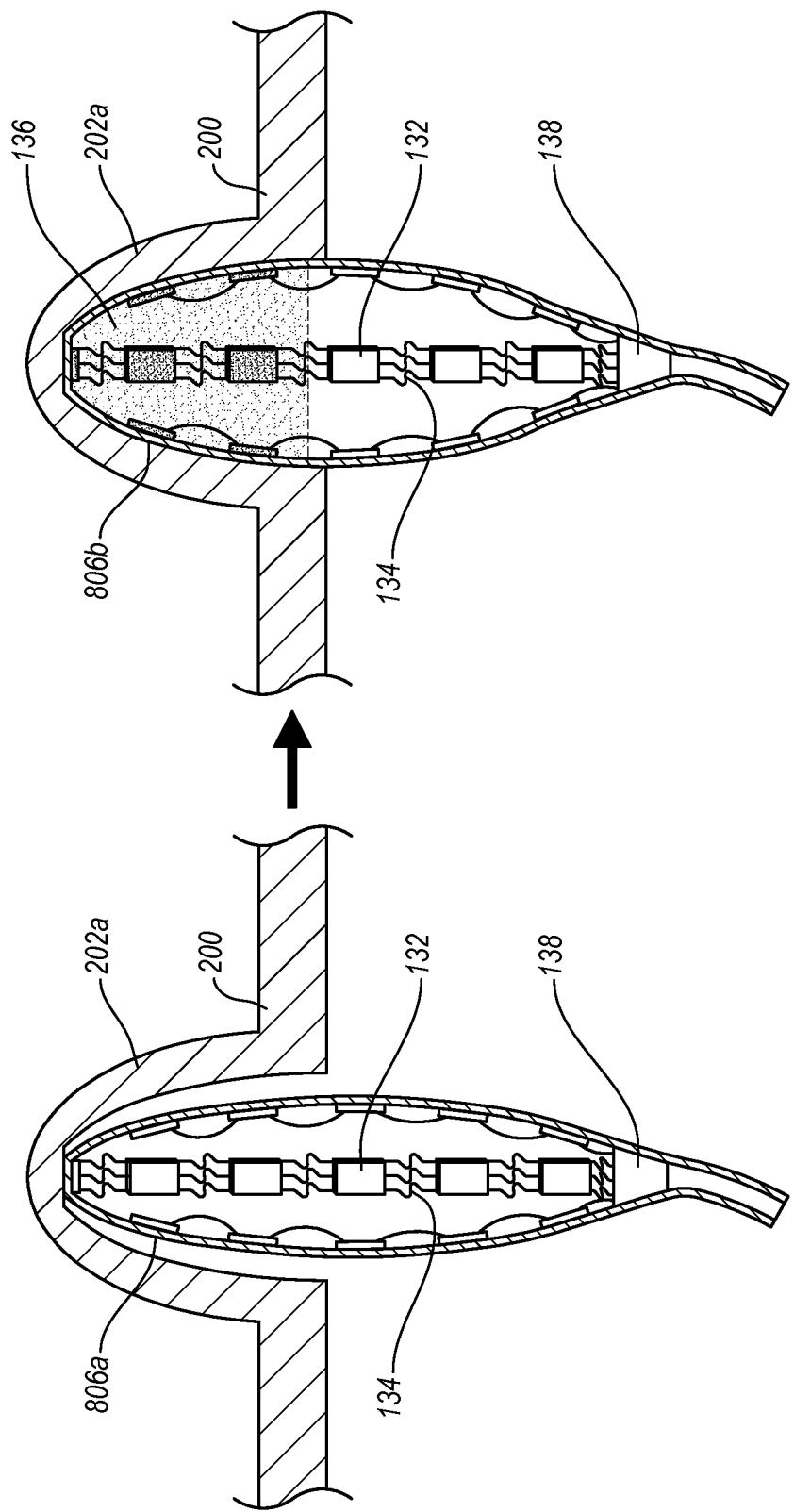
FIGS. 9A and 9B illustrate the apparatus of FIG. 8 positioned in a diverticulum.
Figure 9B:
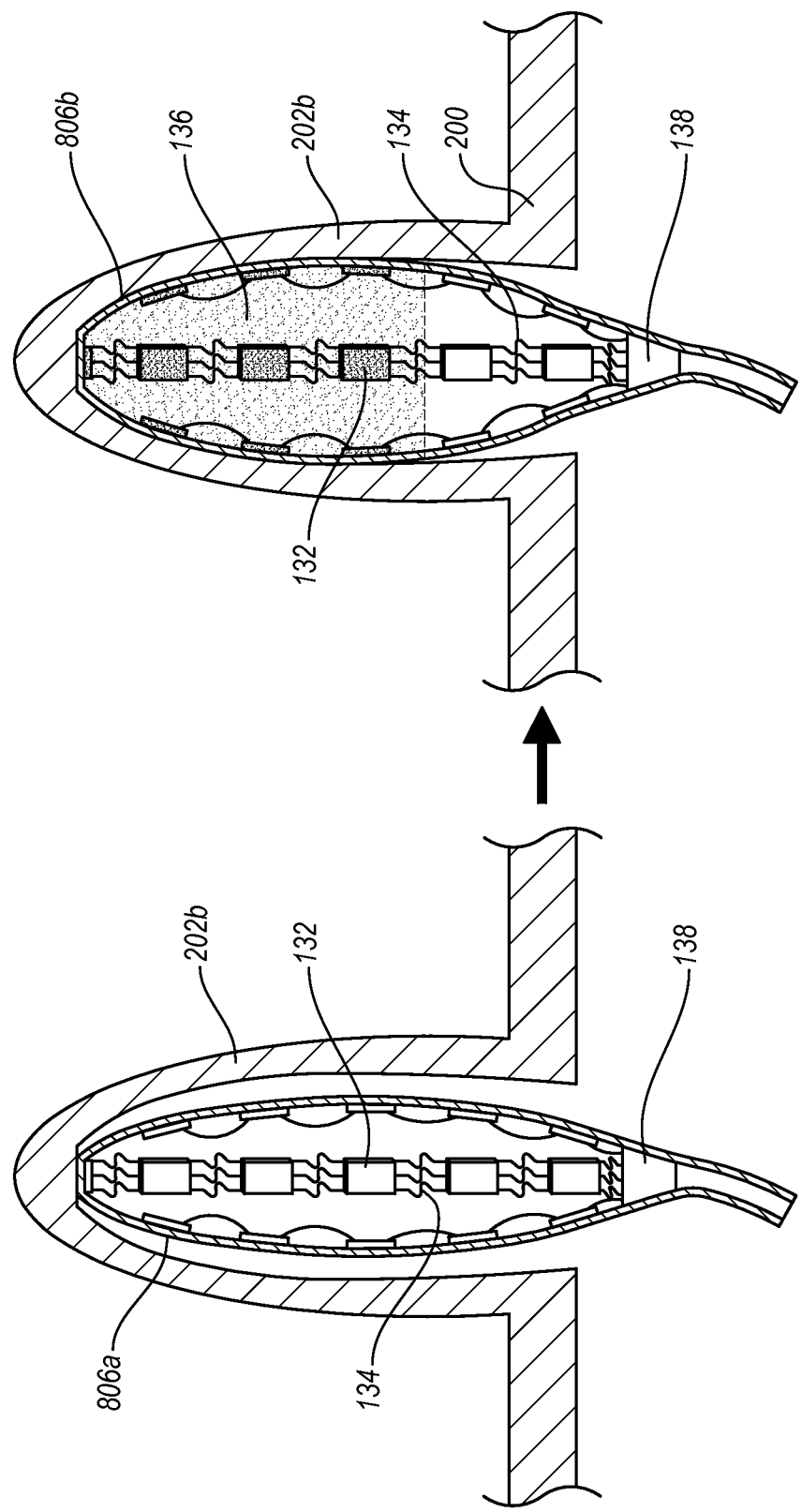

FIGS. 9A and 9B illustrate embodiments of the section of the medical apparatus of FIG. 8 in use, arranged in accordance with at least some embodiments described herein. The balloon-forming chamber 806a may be introduced into diverticula 202a and 202b having different shapes and may be expanded such that outer surfaces of the inflated balloon-forming chamber 806b substantially conform to the contact surfaces within the diverticula 202a and 202b. The size and shape of the inflated balloon-forming chamber 806b may be controlled, for example, by controlling an amount of the air introduced therein.

The temperature may be detected by each of the integrated circuit elements 132 on or within the walls of the inflated balloon-forming chamber 806b. The temperature of each of the integrated circuit elements 132 may be used to determine the region 136 of the inflated balloon-forming chamber 806b in contact with each of the diverticula 202a and 202b. The integrated circuit elements 132 in the region 136 may be used to apply heat to the diverticula 202a and 202b.

Figure 10:
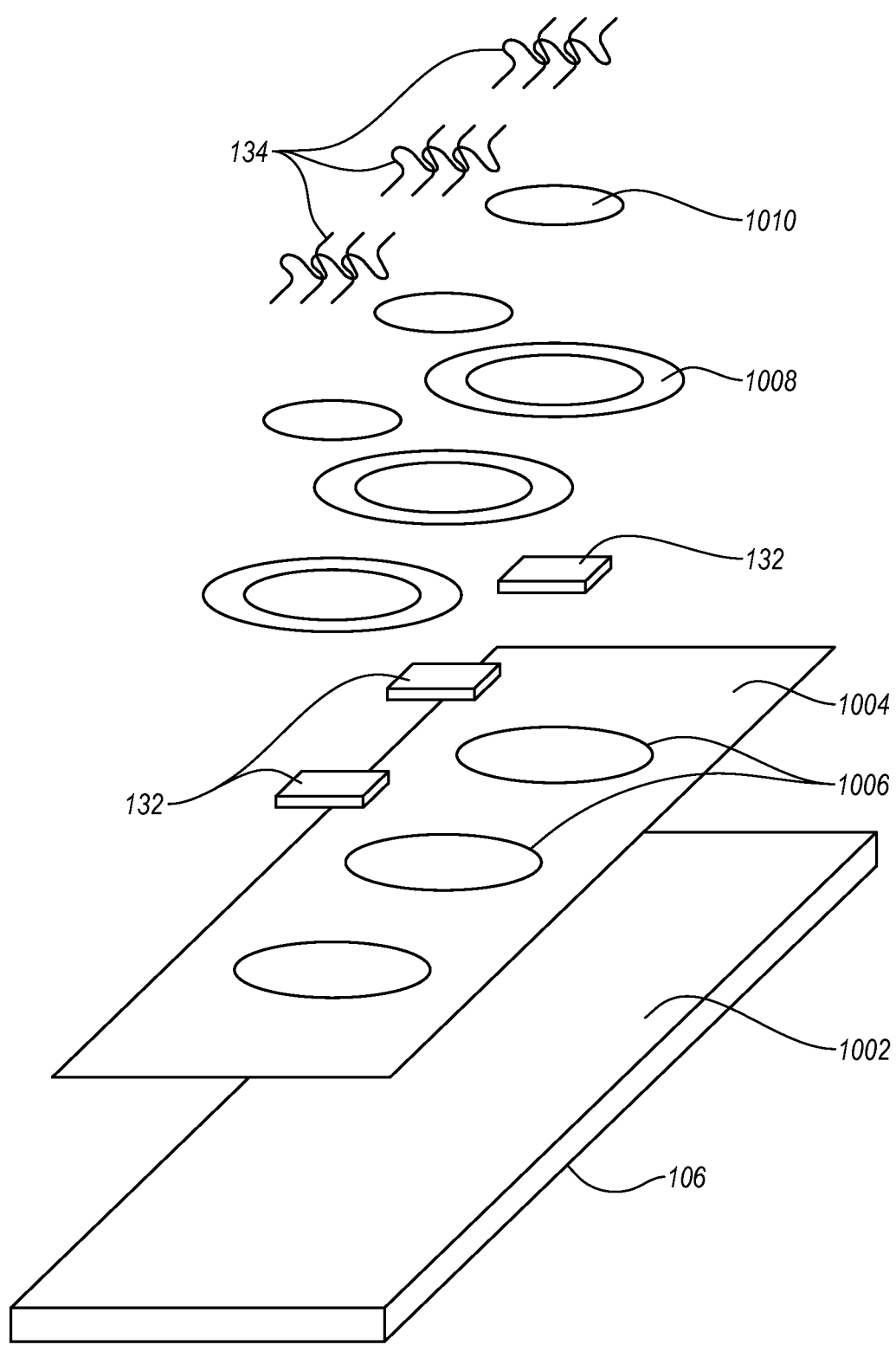
FIG. 10 illustrates an expanded view of an embodiment of an array of the integrated circuit elements.

FIG. 10 illustrates an expanded view of an embodiment of an arrangement of the integrated circuit elements, arranged in accordance with at least some embodiments described herein. The integrated circuit elements 132 may be metal-bonded to thin, circular frames 1006 formed from a metal or metal alloy, such as phosphor bronze. The frames 1006 with the integrated circuit elements 132 bonded thereto may be placed on a sheet 1004 formed of a thin layer of elastic material, such as the same material from which the balloon-forming chamber 106 is formed. The frames 1006 may be sandwiched between thin rings 1008 and the sheet 1004 and the rings 1008 may be bonded to the sheet 1004. An inner diameter of the rings 1008 may be smaller than a diameter of the frames 1006 such that the frames 1006 do not detach even when the balloon-forming chamber 106 expands. The integrated circuit elements 132 may be connected to each other via the interconnects 134, and surfaces of the integrated circuit elements 132 may be covered with a protective coating 1010, such as a gel-like junction resin. The sheet 1004 with the integrated circuit elements 132 positioned thereon may be attached to an interior surface 1002 of the balloon-forming chamber 106.

Figure 11:
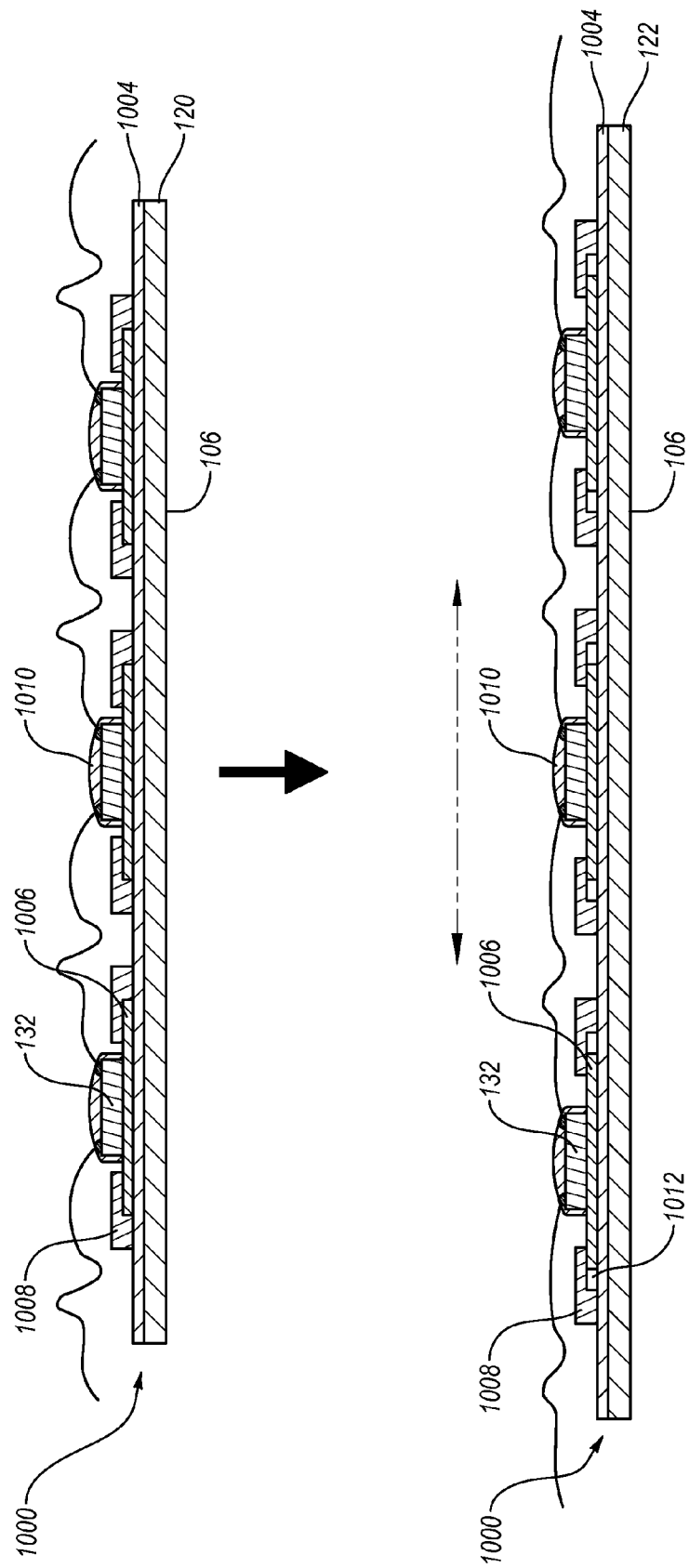
FIG. 11 illustrates a cross-sectional view of the array of the integrated circuit elements of FIG. 10.

FIG. 11 illustrates a cross-sectional view of the integrated circuit elements of FIG. 10, arranged in accordance with at least some embodiments described herein. The elements of FIG. 9 may be assembled to form an array 1000 of the integrated circuit elements 132. The array 1000 may include integrated circuit elements 132, each positioned on one of the frames 1006 which is sandwiched between the sheet 1004 and the rings 1008 to prevent the integrated circuit elements 132 from detaching when the balloon-forming chamber 106 is expanded from the static state 120 to the expanded state 122 resulting in gaps 1012 between the rings 1008 and the frames 1006 on which the integrated circuit elements 132 are positioned.

Figure 12A:
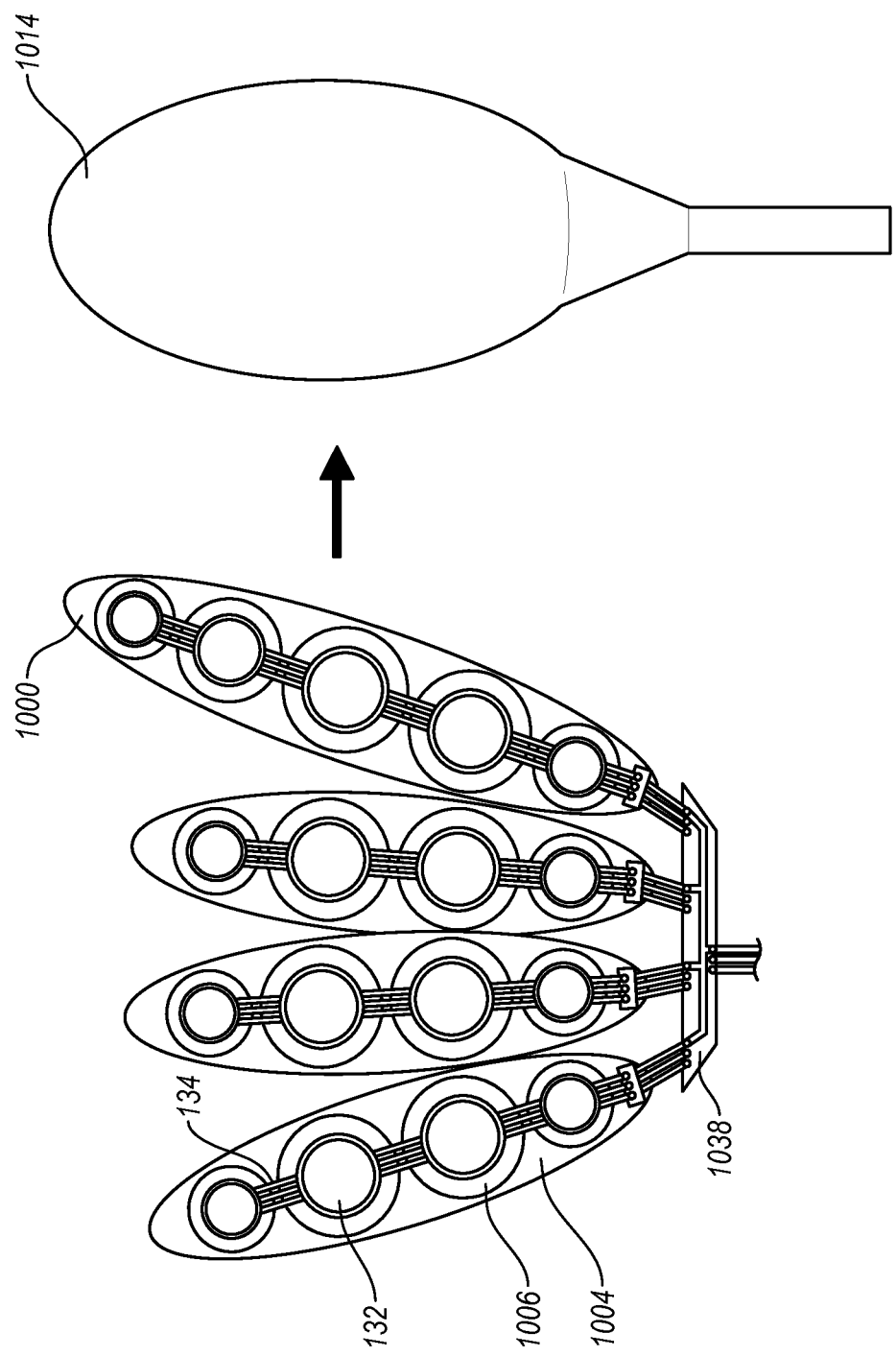
FIGS. 12A and 12B illustrate an embodiment of a method of forming the apparatus.
Figure 12B:
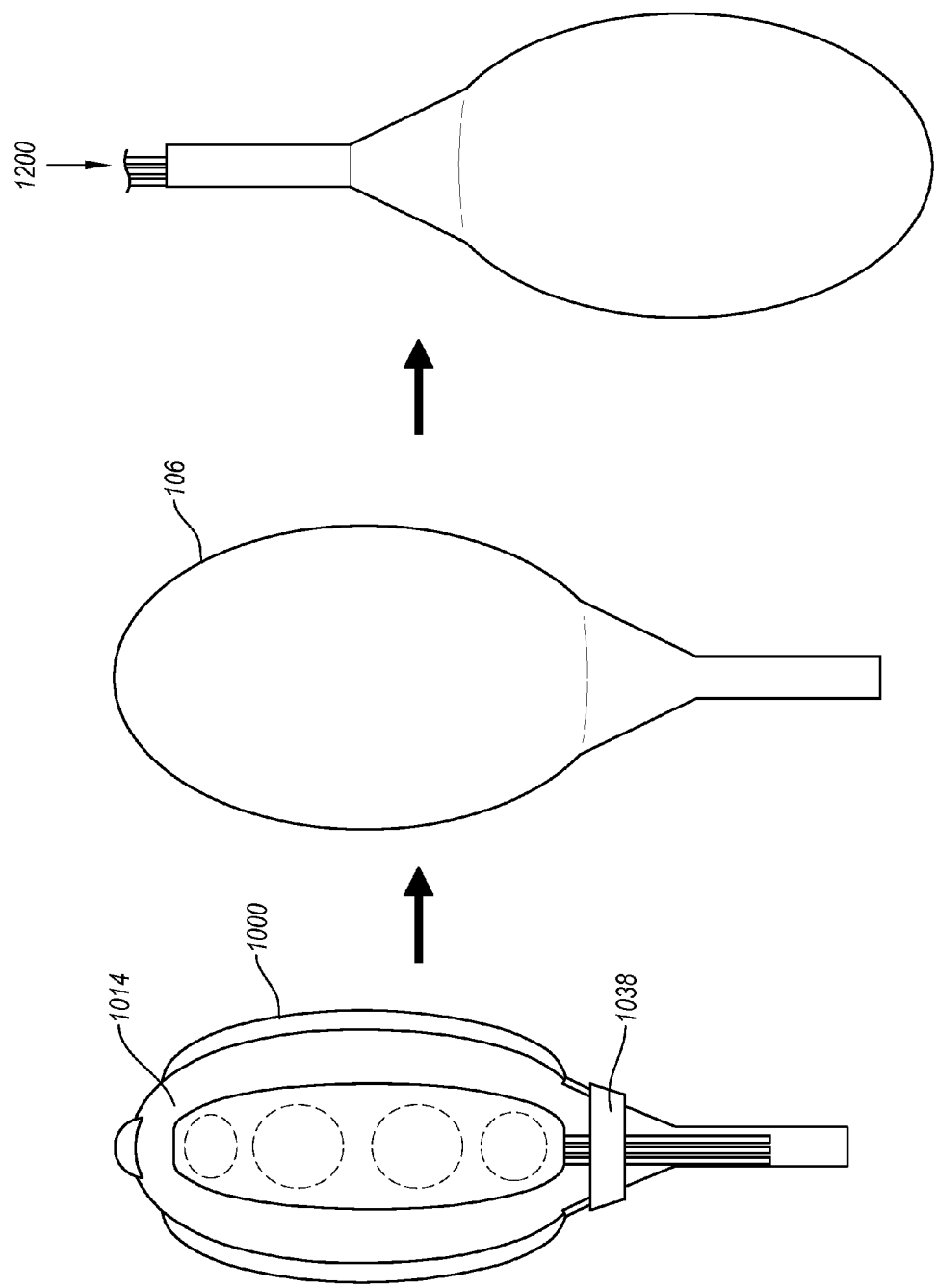

FIGS. 12A and 12B illustrate an embodiment of a method of forming the apparatus, arranged in accordance with at least some embodiments described herein. As shown in FIG. 12A, multiple arrays 1000 of the integrated circuit elements 132 configured to be positioned on the interior surface of the balloon-forming chamber 106 may be formed. The interconnects 134 of each of the arrays 1000 may optionally each be attached to a contact point 1038.

Referring to FIG. 12B, the arrays 1000 may be attached to a mold 1014 sized and configured to form the balloon-forming chamber 106. As a non-limiting example, the mold 1014 may be formed from a material that may be dissolved or otherwise removed with respect to the material used to form the balloon-forming chamber 106, such as a thin resin. The arrays 1000 may be positioned on the mold 1014 such that the integrated circuit elements 132 face the mold 1014 with the sheet 1004 overlying the integrated circuit elements 132. The material used to form the balloon-forming chamber 106 may be formed over exposed surfaces of the arrays 1000 and the mold 1014, and the mold 1014 may be removed to release the balloon-forming chamber 106. In embodiments in which the mold 1014 is formed from the thin resin, an organic solvent 1200 may be introduced into the mold 1014 to dissolve the resin, and a mixture of the resin in the organic solvent may be removed from a hollow interior of the balloon-forming chamber 106. The balloon-forming chamber 106 may be dried and may be attached to the endoscope 102 to form the medical device 100 described with respect to FIG. 1.

Figure 13:
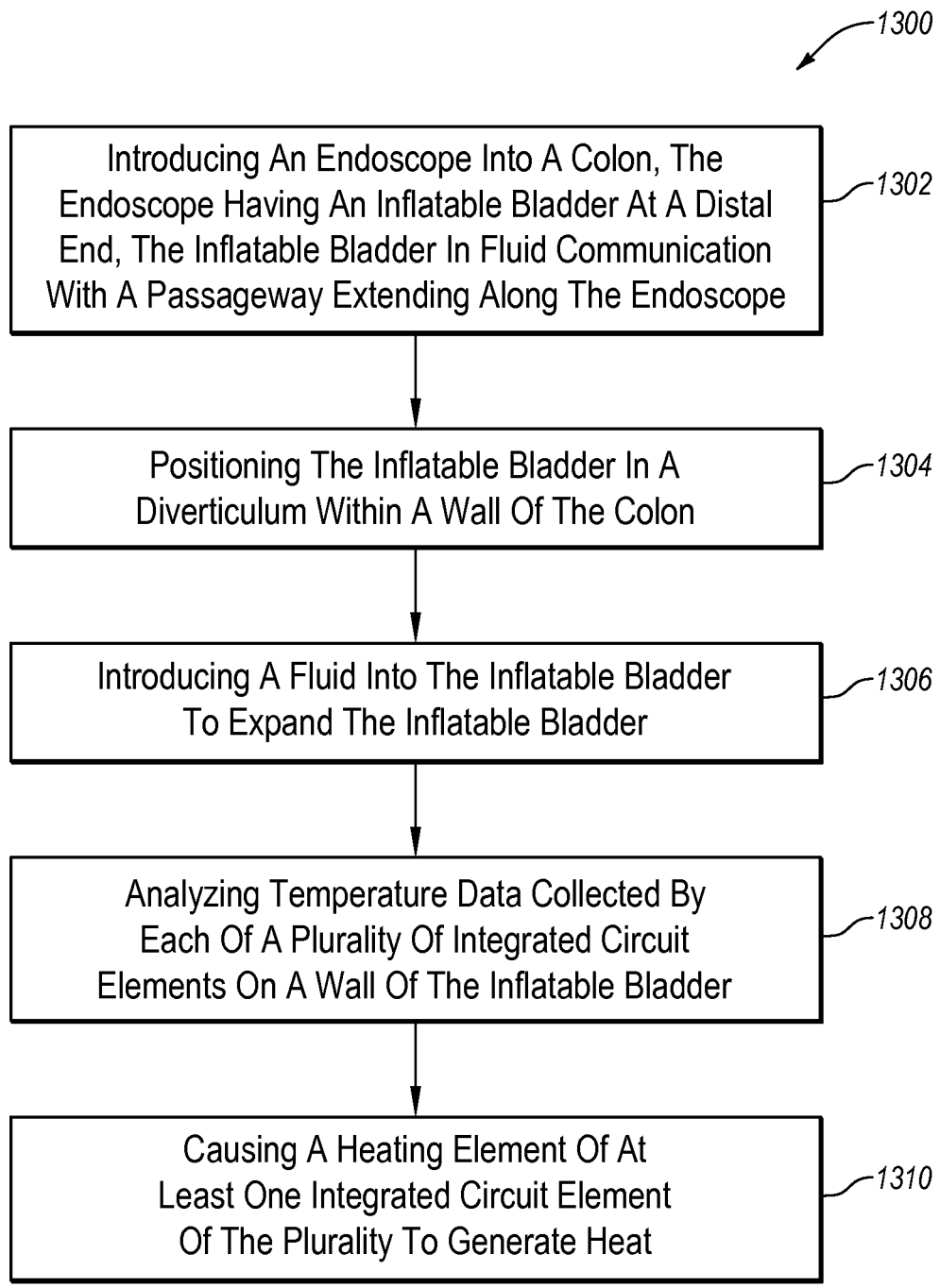
FIG. 13 shows an example flow diagram of a method 1300 for treating diverticula using the medical device of FIG. 1.

FIG. 13 shows an example flow diagram of a method 1300 for treating diverticula using the medical device 100 of FIG. 1, arranged in accordance with at least some embodiments described herein. The method 1300 may be used to determine tissues of a diverticulum that may respond to heat treatment, and to apply localized heat to treat such tissues. The method 1300 may be performed in whole or in part by using the medical apparatus 100, described with respect to FIG. 1. The method 1300 may include various operations, functions, or actions as illustrated by one or more of blocks 1302, 1304, 1306, 1308, and/or 1310. The method 1300 may begin at block 1302.

In block 1302, ["Introducing An Endoscope Into A Colon, The Endoscope Having An Inflatable Bladder At A Distal End, The Inflatable Bladder In Fluid Communication With A Passageway Extending Along The Endoscope"], the method may begin with introducing an endoscope into a colon, the endoscope having an inflatable bladder at a distal end, the inflatable bladder in fluid communication with a passageway extending along the endoscope. For example, the inflatable bladder may be the balloon-forming chamber 106 of the medical device 100. An inner surface of the inflatable bladder may include one or more integrated circuit elements 132 such as those described with respect to FIGS. 3 through 9B, for example. Block 1302 may be followed by block 1304.

In block 1304, ["Positioning The Inflatable Bladder In A Diverticulum Within A Wall Of The Colon"], which may follow block 1302, the inflatable bladder may be positioned within a diverticulum in a wall of the colon. For example, the inflatable bladder may be positioned within the diverticulum using the optical imaging system 110 of the medical device 100 described with respect to FIG. 1. Block 1304 may be followed by block 1306.

In block 1306, ["Introducing A Fluid Into The Inflatable Bladder To Expand The Inflatable Bladder"], which may follow block 1304, a fluid may be introduced into the inflatable bladder to expand the inflatable bladder. The fluid, such as air, may be introduced into the inflatable bladder through the flexible conduit 104 in fluid communication with the inflatable bladder, as shown in FIG. 1. For example, the inflatable bladder may be expanded to conform to a shape of the diverticulum in the colon. Expanding the inflatable bladder within a diverticulum in the colon may cause at least one region of a wall of the inflatable bladder to contact surfaces of the diverticulum. Block 1306 may be followed by block 1308.

In block 1308, ["Analyzing Temperature Data Collected By Each Of A Plurality Of Integrated Circuit Elements On A Wall Of The Inflatable Bladder"], which may follow block 1306, temperature data collected by temperature sensors of each of a plurality of integrated circuit elements on a wall of the inflatable bladder may be analyzed. For example, the temperature data may indicate surfaces of the inflatable bladder in contact with tissue of the diverticulum, or to determine surfaces of the inflatable bladder in contact with inflamed and/or infected tissue of the diverticulum. The integrated circuit elements 132 used to collect the temperature data may include the integrated circuit 400 of FIG. 4, which includes the control circuit 402 including the temperature sensor. The temperature data may be analyzed using, for example, the external device 502 of the computing system 500 described with respect to FIG. 5.

In block 1310, ["Causing A Heating Element Within At Least One Integrated Circuit Element Of The Plurality To Generate Heat"], which may follow block 1308, a heating element within at least one of the integrated circuit elements may be heated. For example, the integrated circuit elements determined to be in contact with the tissue of the diverticulum, as described with respect to block 1308, may be used to generate heat. The integrated circuit elements may each include the integrated circuit 400 described with respect to FIG. 4. The heating element 406 of the integrated circuit 400 may be controlled by the external device 502 described with respect to FIG. 5. As a non-limiting example, the external device 502 may transmit a signal to the integrated circuit 400 to cause the heating element 406 to heat to a temperature of between about 60° C. and about 90° C.

Figure 14:
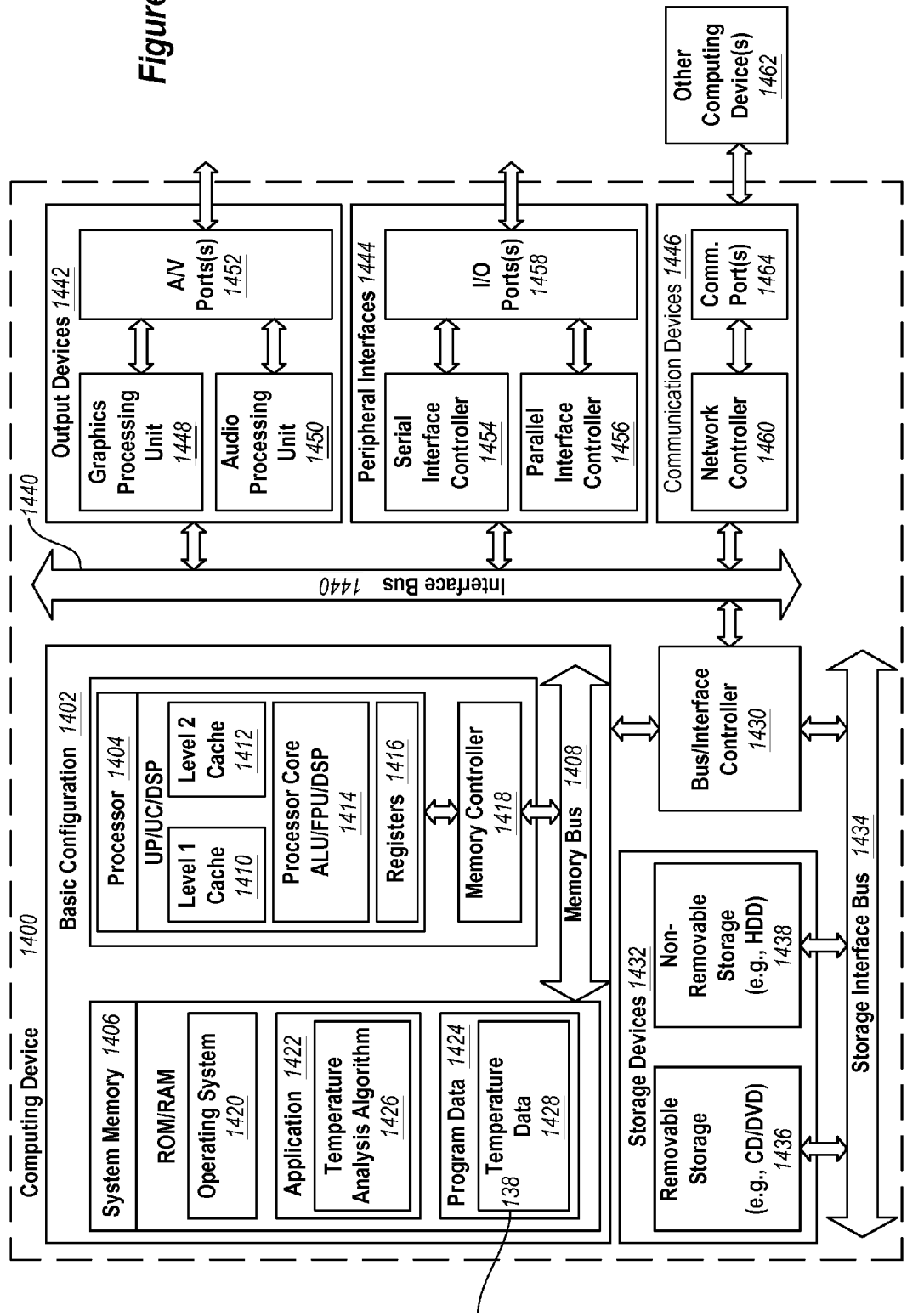
FIG. 14 is a block diagram illustrating an example computing device that is arranged for processing data from one or more integrated circuits and to control the integrated circuits

FIG. 14 is a block diagram illustrating an example computing device 1400 that is arranged for processing data from one or more integrated circuits and to control the integrated circuits based on the processed data in accordance with the present disclosure. In a very basic configuration 1402, computing device 1400 typically includes one or more processors 1404 and a system memory 1406. A memory bus 1408 may be used for communicating between processor 1404 and system memory 1406.

Depending on the desired configuration, processor 1404 may be of any type including, but not limited to, a microprocessor (μP), a microcontroller (μC), a digital signal processor (DSP), or any combination thereof. Processor 1404 may include one or more levels of caching, such as a level one cache 1410 and a level two cache 1412, a processor core 1414, and registers 1416. An example processor core 1414 may include an arithmetic logic unit (ALU), a floating point unit (FPU), a digital signal processing core (DSP Core), or any combination thereof. An example memory controller 1418 may also be used with processor 1404, or in some implementations memory controller 1418 may be an internal part of processor 1404.

Depending on the desired configuration, system memory 1406 may be of any type including, but not limited to, volatile memory (such as RAM), nonvolatile memory (such as ROM, flash memory, etc.) or any combination thereof. System memory 1406 may include an operating system 1420, one or more applications 1422, and program data 1424. Application 1422 may include a temperature analysis algorithm 1426 that is arranged to perform the functions as described herein including those described with respect to the method 1300 of FIG. 13. Program data 1424 may include temperature data 1428 that may be useful for receiving and processing temperature data from one or more integrated circuits and to control the integrated circuits based on the processed temperature data as is described herein. In some embodiments, application 1422 may be arranged to operate with program data 1424 on operating system 1420 such that implementations of treating diverticula may be provided as described herein. This described basic configuration 1402 is illustrated in FIG. 14 by those components within the inner dashed line.

Computing device 1400 may have additional features or functionality, and additional interfaces to facilitate communications between basic configuration 1402 and any required devices and interfaces. For example, a bus/interface controller 1430 may be used to facilitate communications between basic configuration 1402 and one or more data storage devices 1432 via a storage interface bus 1434. Data storage devices 1432 may be removable storage devices 1436, non-removable storage devices 1438, or a combination thereof. Examples of removable storage and non-removable storage devices include magnetic disk devices such as flexible disk drives and hard-disk drives (HDD), optical disk drives such as compact disk (CD) drives or digital versatile disk (DVD) drives, solid state drives (SSD), and tape drives to name a few. Example computer storage media may include volatile and nonvolatile, removable and non-removable media implemented in any method or technology for storage of information, such as computer-readable instructions, data structures, program modules, or other data.

System memory 1406, removable storage devices 1436 and non-removable storage devices 1438 are examples of computer storage media. Computer storage media includes, but is not limited to, RAM, ROM, EEPROM, flash memory or other memory technology, CD-ROM, digital versatile disks (DVD) or other optical storage, magnetic cassettes, magnetic tape, magnetic disk storage or other magnetic storage devices, or any other medium which may be used to store the desired information and which may be accessed by computing device 1400. Any such computer storage media may be part of computing device 1400.

Computing device 1400 may also include an interface bus 1440 for facilitating communication from various interface devices (e.g., output devices 1442, peripheral interfaces 1444, and communication devices 1446) to basic configuration 1402 via bus/interface controller 1430. Example output devices 1442 include a graphics processing unit 1448 and an audio processing unit 1450, which may be configured to communicate to various external devices such as a display or speakers via one or more A/V ports 1452. Example peripheral interfaces 1444 include a serial interface controller 1454 or a parallel interface controller 1456, which may be configured to communicate with external devices such as input devices (e.g., keyboard, mouse, pen, voice input device, touch input device, etc.) or other peripheral devices (e.g., printer, scanner, etc.) via one or more I/O ports 1458. An example communication device 1446 includes a network controller 1460, which may be arranged to facilitate communications with one or more other computing devices 1462 over a network communication link via one or more communication ports 1464.

The network communication link may be one example of a communication media. Communication media may typically be embodied by computer-readable instructions, data structures, program modules, or other data in a modulated data signal, such as a carrier wave or other transport mechanism, and may include any information delivery media. A "modulated data signal" may be a signal that has one or more of its characteristics set or changed in such a manner as to encode information in the signal. By way of example, and not limitation, communication media may include wired media such as a wired network or direct-wired connection, and wireless media such as acoustic, radio frequency (RF), microwave, infrared (IR) and other wireless media. The term "computer-readable media" as used herein may include both storage media and communication media.

Computing device 1400 may be implemented as a portion of a small-form factor portable (or mobile) electronic device such as a cell phone, a personal data assistant (PDA), a personal media player device, a wireless web-watch device, a personal headset device, an application-specific device, or a hybrid device that includes any of the above functions. Computing device 1400 may also be implemented as a personal computer including both laptop computer and non-laptop computer configurations.

The present disclosure is not to be limited in terms of the particular embodiments described herein, which are intended as illustrations of various aspects. Many modifications and variations can be made without departing from its spirit and scope, as will be apparent to those skilled in the art. Functionally-equivalent methods and apparatuses within the scope of the disclosure, in addition to those enumerated herein, will be apparent to those skilled in the art from the foregoing descriptions. Such modifications and variations are intended to fall within the scope of the appended claims. The present disclosure is to be limited only by the terms of the appended claims, along with the full scope of equivalents to which such claims are entitled. It is to be understood that the present disclosure is not limited to particular methods, reagents, compounds, compositions, or biological systems, which can, of course, vary. It is also to be understood that the terminology used herein is for the purpose of describing particular embodiments only, and is not intended to be limiting.

With respect to the use of substantially any plural and/or singular terms herein, those having skill in the art can translate from the plural to the singular and/or from the singular to the plural as is appropriate to the context and/or application. The various singular/plural permutations may be expressly set forth herein for sake of clarity.

It will be understood by those within the art that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to embodiments containing only one such recitation, even when the same claim includes the introductory phrases "one or more" or "at least one" and indefinite articles such as "a" or "an" (e.g., "a" and/or "an" should be interpreted to mean "at least one" or "one or more"); the same holds true for the use of definite articles used to introduce claim recitations. In addition, even if a specific number of an introduced claim recitation is explicitly recited, those skilled in the art will recognize that such recitation should be interpreted to mean at least the recited number (e.g., the bare recitation of "two recitations," without other modifiers, means at least two recitations, or two or more recitations). Furthermore, in those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense one having skill in the art would understand the convention (e.g., "a system having at least one of A, B, or C" would include but not be limited to systems that have A alone, B alone, C alone, A and B together, A and C together, B and C together, and/or A, B, and C together, etc.). It will be further understood by those within the art that virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B."

In addition, where features or aspects of the disclosure are described in terms of Markush groups, those skilled in the art will recognize that the disclosure is also thereby described in terms of any individual member or subgroup of members of the Markush group.

As will be understood by one skilled in the art, for any and all purposes, such as in terms of providing a written description, all ranges disclosed herein also encompass any and all possible subranges and combinations of subranges thereof. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third, and upper third, etc. As will also be understood by one skilled in the art, all language such as "up to," "at least," and the like include the number recited and refer to ranges which can be subsequently broken down into subranges as discussed above. Finally, as will be understood by one skilled in the art, a range includes each individual member. Thus, for example, a group having 1-3 cells refers to groups having 1, 2, or 3 cells. Similarly, a group having 1-5 cells refers to groups having 1, 2, 3, 4, or 5 cells, and so forth.

From the foregoing, it will be appreciated that various embodiments of the present disclosure have been described herein for purposes of illustration, and that various modifications may be made without departing from the scope and spirit of the present disclosure. Accordingly, the various embodiments disclosed herein are not intended to be limiting, with the true scope and spirit being indicated by the following claims.

The invention claimed is:

1. An apparatus for treating diverticula, comprising:
    a flexible conduit having a proximal end, a distal end, and a passageway therethrough;
    a balloon-forming chamber at the distal end of the flexible conduit; and
    a plurality of integrated circuit elements positioned on walls of the balloon-forming chamber to provide heat for treatment of diverticula.

2. The apparatus of claim 1, wherein each of the integrated circuit elements includes a temperature sensor configured to detect a temperature of tissues in a region proximate the integrated circuit element, a control circuit configured to detect a temperature of a surface of the balloon-forming chamber adjacent the integrated circuit element, and a heating element configured to generate heat based on the temperature of the surface of the balloon-forming chamber.

3. The apparatus of claim 2, wherein the heating element includes at least one metal-oxide-semiconductor field-effect transistor.

4. The apparatus of claim 1, wherein the plurality of integrated circuit elements are distributed across the walls on an interior surface of the balloon-forming chamber.

5. The apparatus of claim 1, wherein each of the integrated circuit elements is positioned on a circular frame positioned between a ring and a sheet of elastic material.

6. The apparatus of claim 1, wherein the balloon-forming chamber is formed from at least one of silicone rubber and an elastic, heat-resistant and biocompatible polymer.

7. The apparatus of claim 1, further comprising:
    an endoscope;
    the flexible conduit having the passageway being configured as a hollow interior chamber extending along at least a portion of a length of the endoscope;
    the balloon-forming chamber positioned at a distal end of the endoscope, an opening of the balloon-forming chamber in communication with the hollow interior chamber of the conduit; and
    the plurality of integrated circuit elements positioned on surfaces of the walls of the balloon-forming chamber, each of the integrated circuits of the plurality including at least one heating element and a temperature sensor.

8. The apparatus of claim 7, wherein the endoscope further includes an optical imaging system positioned at the distal end of the endoscope, wherein the distal end of the endoscope is configured for introduction into a cavity of a body.

9. The apparatus of claim 7, wherein the balloon-forming chamber is sized and configured to expand to substantially conform to surfaces of a diverticulum within a colon.

10. The apparatus of claim 7, wherein the temperature sensor is configured to determine a temperature of tissue in contact with an outer surface of the balloon-forming chamber.

11. The apparatus of claim 7, wherein the at least one heating element includes a metal-oxide-semiconductor field-effect transistor or a semiconductor switching element.

12. The apparatus of claim 7, wherein each of the integrated circuit elements of the plurality includes a single, monolithic integrated circuit chip having the at least one heating element, the temperature sensor, a control circuit, and a current sensing resistor and is electrically coupled with at least one adjacent integrated circuit element of the plurality by conductive interconnects.

13. The apparatus of claim 12, wherein each of the conductive interconnects has a length greater than a distance between adjacent, electrically coupled integrated circuit elements of the plurality to accommodate expansion of the balloon-forming chamber.

14. The apparatus of claim 7, wherein the plurality of integrated circuit elements are communicatively coupled with at least one external device configured to analyze temperature data and control the at least one heating element based on a temperature of the surfaces of the balloon-forming chamber adjacent the at least one heating element.

15. A method for treating diverticula, comprising:
    introducing the apparatus of claim 7 into a colon;
    positioning the balloon-forming chamber in a diverticulum within a wall of the colon;
    introducing a fluid into the balloon-forming chamber to expand the balloon-forming chamber;
    analyzing temperature data collected by each of a plurality of integrated circuit elements on a wall of the balloon-forming chamber; and
    causing a heating element of at least one integrated circuit element in the at least one region to generate heat.

16. The method of claim 15, wherein positioning the balloon-forming chamber in a diverticulum within a wall of the colon comprises using an optical imaging system of the endoscope to position the balloon-forming chamber.

17. The method of claim 15, wherein introducing a fluid into the balloon-forming chamber to expand the balloon-forming chamber comprises expanding the balloon-forming chamber within a diverticulum in the colon to cause at least one region of the wall of the balloon-forming chamber to contact surfaces of the diverticulum.

18. The method of claim 15, wherein analyzing temperature data comprises determining contact between at least one region of the balloon-forming chamber and inflamed or infected tissue of the diverticulum.

19. The method of claim 15, wherein causing a heating element within at least one integrated circuit element of the plurality to generate heat comprises causing the heating element to heat to a temperature of between about 60° C. and about 90° C.

20. The method of claim 15, wherein causing a heating element within at least one integrated circuit element of the plurality to generate heat comprises transmitting a signal to the at least one integrated circuit element from an external device communicatively coupled with each of the plurality of integrated circuit elements.

* * * * *

UNITED STATES PATENT AND TRADEMARK OFFICE
CERTIFICATE OF CORRECTION

PATENT NO. : 9,204,993 B2  
APPLICATION NO. : 13/991405  
DATED : December 8, 2015  
INVENTOR(S) : Mihara Page 1 of 1

It is certified that error appears in the above-identified patent and that said Letters Patent is hereby corrected as shown below:

IN THE DRAWINGS

In Fig. 14, Sheet 15 of 15, delete "UP/UC/DSP" and insert -- µP/µC/DSP --, therefor.

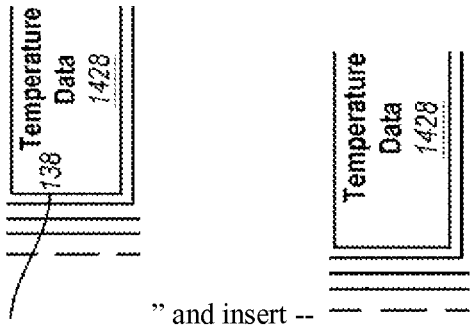

In Fig. 14, Sheet 15 of 15, delete " " and insert -- --, therefor.

IN THE SPECIFICATION

In Column 1, below Title, Line 1, insert -- CROSS-REFERENCE TO RELATED APPLICATION
This Application is the U.S. National Stage filing under 35 U.S.C. § 371 of PCT Application No. PCT/US13/21592 filed on January 15, 2013. --.

In Column 8, Line 7, delete "power line 414" and insert -- power line 514 --, therefor.

In Column 10, Line 5, delete "133b," and insert -- 132b, --, therefor.

In Column 10, Line 9, delete "133b," and insert -- 132b, --, therefor.

In Column 12, Line 52, delete "medical apparatus" and insert -- medical device --, therefor.

Signed and Sealed this  
Twenty-sixth Day of April, 2016

Michelle K. Lee  
*Director of the United States Patent and Trademark Office*